United States Patent
Ram et al.

(10) Patent No.: US 10,975,131 B2
(45) Date of Patent: Apr. 13, 2021

(54) FACTOR H-FC IMMUNOTHERAPHY

(71) Applicant: University of Massachusetts, Boston, MA (US)

(72) Inventors: Sanjay Ram, Worcester, MA (US); Douglas T. Golenbock, Wellesley, MA (US); Alberto Visintin, Natick, MA (US); Jutamas Shaughnessy, Carlisle, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 15/770,965

(22) PCT Filed: Oct. 27, 2016

(86) PCT No.: PCT/US2016/059072
§ 371 (c)(1),
(2) Date: Apr. 25, 2018

(87) PCT Pub. No.: WO2017/075189
PCT Pub. Date: May 4, 2017

(65) Prior Publication Data
US 2018/0305425 A1    Oct. 25, 2018

Related U.S. Application Data

(60) Provisional application No. 62/246,662, filed on Oct. 27, 2015.

(51) Int. Cl.
*C07K 14/47*      (2006.01)
*A61P 31/04*      (2006.01)
*A61K 38/00*      (2006.01)

(52) U.S. Cl.
CPC ........... *C07K 14/472* (2013.01); *A61P 31/04* (2018.01); *A61K 38/00* (2013.01); *C07K 2319/20* (2013.01); *C07K 2319/30* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,438,114 A | 3/1984 | Boberg et al. | |
| 5,578,572 A | 11/1996 | Horwitz et al. | |
| 5,643,570 A | 7/1997 | Theofan et al. | |
| 6,107,076 A | 8/2000 | Tang et al. | |
| 6,462,254 B1 | 10/2002 | Vemachio et al. | |
| 6,569,112 B2 | 5/2003 | Strahilevitz | |
| 6,660,843 B1 | 12/2003 | Feige et al. | |
| 7,157,418 B1 | 1/2007 | McDonald et al. | |
| 8,080,245 B2 | 12/2011 | Visintin et al. | |
| 8,889,374 B2* | 11/2014 | Schmidt ............... | C07K 14/472 435/69.1 |
| 2003/0032090 A1 | 2/2003 | Hardiman et al. | |
| 2003/0049648 A1 | 3/2003 | Choi | |
| 2013/0078245 A1 | 3/2013 | Holers et al. | |
| 2015/0099297 A1 | 4/2015 | Tryggvason et al. | |
| 2015/0139975 A1* | 5/2015 | Schmidt ............... | C07K 14/472 424/94.5 |
| 2016/0184458 A1* | 6/2016 | Heartlein ............... | C12N 15/00 514/44 R |
| 2018/0214531 A1* | 8/2018 | Biolchi ............... | A61K 39/095 |
| 2018/0305425 A1* | 10/2018 | Ram ..................... | C07K 14/472 |
| 2019/0031750 A1* | 1/2019 | Koenig ................. | A61K 47/60 |
| 2019/0071477 A1* | 3/2019 | Bao ........................ | C12N 15/62 |
| 2019/0100581 A1* | 4/2019 | Koenig ................. | A61K 47/60 |

FOREIGN PATENT DOCUMENTS

| | | | |
|---|---|---|---|
| WO | WO 2004/103294 | 12/2004 | |
| WO | WO 2006/025995 | 3/2006 | |
| WO | WO 2007/001332 | 1/2007 | |
| WO | WO 2015/055991 | 4/2015 | |
| WO | WO-2015055991 A1 * | 4/2015 | |
| WO | WO-2017075189 A1 * | 5/2017 | ........... C07K 14/472 |
| WO | WO-2017114401 A1 * | 7/2017 | ............. C12N 15/62 |

OTHER PUBLICATIONS

Konar et al, PLoS One, 2015, 10/6:e0128185 18 pages. published: Jun. 9, 2015 (Year: 2015).*
Shaughnessy et al, Journal Biological Chemistry, Jun. 24, 2011, 286/25:22235-22242. (Year: 2011).*
Shaughnessy et al, Journal Immunology, 2016, 196:1732-1740. prepublished online: Jan. 15, 2016 (Year: 2016).*
Meri et al, PLoS Pathogens, 2013, 9/4:e1003308, 12 pages. published: Apr. 18, 2013 (Year: 2013).*
Rodriguez et al, Bioscience Reports, 2014, 34/art:e00146. 15 pages (Year: 2014).*
Ripoche et al Biochemical Journal, Jan. 15, 1988, 249/2:593-602. (Year: 1988).*
Shaughnessy et al (Abstracts/Immunobiology, 217 (2012): 1131. Abstract #7). (Year: 2012).*
International Search Report and Written Opinion in International Application No. PCT/US2016/59072, dated Jan. 9, 2017, 13 pages.
Abrahamson et al., "Biochemical characterization of recombinant fusions of lipopolysaccharide binding protein and bactericidal/permeability-increasing protein. Implications in biological activity," Journal of Biological Chemistry, 272:2149-2155 (1997).
Akashi et al., "Lipopolysaccharide interaction with cell surface Toll-like receptor 4-MD 2: higher affinity than that with MD 2 or CD14," J. Exg. Med., 198:1035 (2003).
Apicella et al., "Modification by sialic acid of Neisseria gonorrhoeae lipooligosaccharide epitope expression in human urethral exudates: an immunoelectron microscopic analysis," J Infect Dis, 162: 506-512 (1990).

(Continued)

*Primary Examiner* — Nita M. Minnifield
(74) *Attorney, Agent, or Firm* — Fish & Richardson P.C.

(57) ABSTRACT

Fusion proteins comprising human FH domains 18-20 (FH18-20) linked via an optional linker to IgG Fc, wherein the FH has mutation of D to G at position 1119 in domain 19; FHD1119G/Fc), and methods of use thereof, e.g., to treat pathogen infections.

9 Claims, 11 Drawing Sheets
Specification includes a Sequence Listing.

(56) References Cited

OTHER PUBLICATIONS

Arko et al., "Binding of S protein by Neisseria gonorrhoeae and potential role in invasion," J Clin Microbiol, 29: 70-75 (1991).
Ashkenazi et al., "Immunoadhesins as research tolls and therapeutic agents," Curr. Opin. Immunol, 9(2):195-200 (1997).
Bassler et al., "How bacteria talk to each other: regulation of gene expression by quorum sensing," Current Opinion in Microbiology, 2:582-587 (1999).
Bazil and Strominger, "Shedding as a mechanism of down-modulation ofCD14 on stimulated human monocytes," J. Immunol., 147:1567-1574 (1991).
Bazil et al., "Biochemical characterization of a soluble form of the 53-kDa monocyte surface antigen," Eur. J. Immunol., 16:1583-1589 (1986).
Beamer et al., "The BPI/LBP family of proteins: a structural analysis of conserved regions," Protein Science, 7:906-914 (1998).
Bell et al., "Leucine-rich repeats and pathogen recognition in Toll-like receptors," Trends Immunology, 24(10):528-533 (2003).
Bell et al., "The molecular structure of the Toll-like receptor 3 ligand-binding domain," PNAS, 102(31):10976-10980 (2005).
Beutler, "Inferences, questions and possibilities in Toll-like receptor signalling," Nature, 430:257 (2004).
Blaum et al., "Structural basis for sialic acid-mediated self-recognition by complement factor H," Nat Chem Biol, 11: 77-83 (2015).
Blom et al., "Complement evasion strategies of pathogens-acquisition of inhibitors and beyond," Mal Immunal, 46: 2808-2817 (2009).
Brinkman-Van der Linden et al., "Loss of N-glycolylneuraminic acid in human evolution. Implications for sialic acid recognition by siglecs," J Biol Chem, 275: 8633-8640 (2000).
Bufler et al., "Soluble lipopolysaccharide receptor (CD14) is released via two different mechanisms from human monocytes and CD14 transfectants," Eur. J. Immunol., 25:604-610 (1995).
Camara et al., "Molecular characterization of two high-level ceftriaxone-resistant Neisseria gonorrhoeae isolates detected in Catalonia, Spain," J Antimicrob Chemother, 67: 1858-1860 (2012).
CDC, "Antibiotic resistance threats in the United States, 2013," Department of Health and Human Services, Centers for Disease Control and Prevention, 114 pages (2013).
Chamow and Ashkenazi, "Immunoadhesins: principles and applications," Trends Biotechnol, 14(2):52-60 (1996).
Chmura et al., "Painful Lymphadenopathy and Fulminant Sepsis in a Previously Healthy 16-Year-Old Girl," Chest, 124: 379-382 (2003).
Chou et al., "A mutation in human CMP-sialic acid hydroxylase occurred after the Homo-Pan divergence," PNAS, 95: 11751-11756 (1998).
Chou et al., "Inactivation of CMP-Nacetylneuraminic acid hydroxy lase occurred prior to brain expansion during human Evolution," PNAS, 99: 11736-11741 (2002).
Davies and Varki. "Why Is N-Glycolylneuraminic Acid Rare in the Vertebrate Brain?," Top Curr Chem, 366: 31-54 (2015).
De Cordoba et al., "Complement dysregulation and disease: from genes and proteins to diagnostics and drugs," Immunobiology, 217: 1034-1046 (2012).
Dehio et al., "Vitronectin-dependent invasion of epithelial cells by Neisseria gonorrhoeae involves alpha(v) integrin receptors," FEES Lett, 424: 84-88 (1998).
Duensing and van Putten, "Vitronectin mediates internalization of Neisseria gonorrhoeae by Chinese hamster ovary cells," Infect Immun, 65: 964-970 (1997).
Fearon and Austen, "Activation of the alternative complement pathway due to resistance of zymosan-bound amplification convertase to endogenous regulatory mechanisms," PNAS, 74: 1683-1687 (1977).
Ferreira et al., "The binding of factor H to a complex of physiological poly anions and C3b on cells is impaired in atypical hemolytic uremic syndrome," J Immunol, 182: 7009-7018 (2009).

Fitzgerald et al., "LPS-TLR4 signaling to IRF-3/7 and NF-kappaB involves the toll adapters TRAM and TRIF," J. Exp. Med., 198: 1043-55 (2003).
Froidevaux et al., "Anti-Toll-Like Receptor 4 (TLR4) Antibodies Protect from Lethal Endotoxemia but Not from Gram-Negative Septice Shock," Gateway to the National Library of Medicine, [printed from http://gateway.nlm.nih.gov/MeetingAbstracts/102265282.htrnl on Jan. 25, 20081, 2 pages.
Gangloff et al., "MD 2: the Toll 'gatekeeper' in endotoxin signalling," Trends Biochem. Sci., 29:294 (2004).
Gioannini et al., "Isolation of an endotoxin-MD-2 complex that produces Toll-like receptor 4-dependent cell activation at picomolar concentrations," PNAS, 101:4186-4191 (2004).
Goldbach-Mansky and Lipsky, "New Concepts in the Treatment of Rheumatoid Arthritis," Annu. Rev. Med., 55:197-216 (2003).
Gomez-Duarte et al., "Binding of vitronectin to opa-expressing Neisseria gonorrhoeae mediates invasion ofHeLa cells," Infect Immun, 65: 3857-3866 (1997).
Gray-Owen et al., "CD66 carcinoembryonic antigens mediate interactions between Opa-expressing Neisseria gonorrhoeae and human polymorphonuclear phagocytes," EMBO J, 16: 3435-3445 (1997).
Gruber et al., "Structural model of MD 2 and functional role of its basic amino acid clusters involved in cellular lipopolysaccharide recognition," J. Biol. Chem., 279:28475 (2004).
Gulati et al., "Enhanced factor H binding to sialylated Gonococci is restricted to the sialylated lacto-N-neotetraose lipooligosaccharide species: implications for serum resistance and evidence for a bifunctional lipooligosaccharide sialyltransferase in Gonococci," Infect Immun, 73: 7390-7397 (2005).
Gulati et al "Immunization against a Saccharide Epitope Accelerates Clearance of Experimental Gonococcal Infection," PLoS Pathog, 9: e1003559 (2013).
Gulati et al., "Properdin is critical for antibody-dependent bactericidal activity against Neisseria gonorrhoeae that recruit C4b-binding protein," J Immunol, 188: 3416-3425 (2012).
Haziot et al., "Neutrophil CD14: biochemical properties and role in the secretion of tumor necrosis factor-alpha in response to lipopolysaccharide," J. Immunol., 150:5556-5565 (1998).
Haziot et al., "The monocyte differentiation antigen, CD14, is anchored to the cell membrane by a phosphatidylinositol linkage," J. Immunol., 141:547-552 (1988).
Hitchcock et al., "Analyses of gonococcal H.8 antigen: surface location, inter- and intrastrain electrophoretic heterogeneity, and unusual two- dimensional electrophoretic characteristics," J Exp. Med, 162:2017-2034 (1985).
Hurley, "Endotoxemia: Methods of Detection and Clinical Correlates," Clinical Microbiology Reviews, 1995, 8(2):268-292 (1995).
Hyakushima et al., "Interaction of soluble form of recombinant extracellular TLR4 domain with C15 MD-2 enables lipopolysaccharide binding and attenuates TLR4-mediated signaling," J. Immunol., 173(11 ):6949-6954 (2004).
Inohara et al., "ML—a conserved domain involved in innate immunity and lipid metabolism," Trends Biochem. Sci., 27:219 (2002).
International Preliminary Report on Patentability in International Application No. PCT/US2016/59072, dated May 11, 2018.
Jack et al., "Lipopolysaccharide-binding protein is required to combat a murine gram-negative bacterial infection," Nature, 389:742 (1997).
Jerse et al., "Estradiol-Treated Female Mice as Surrogate Hosts for Neisseria gonorrhoeae Genital Tract Infections," Front Microbiol, 2: 107 (2011).
Jit et al., "TNF-alpha neutralization in cytokine-driven diseases: a mathematical model to account for therapeutic success in rheumatoid arthritis but therapeutic failure in systemic inflammatory response syndrome," Rheumatology, 44:323-331 (2005).
Jokiranta et al., "Each of the three binding sites on complement factor H interacts with a distinct site on C3b," J Biol Chem, 275: 27657-27662 (2000).
Juan et al., "Soluble CD14 truncated at amino acid 152 binds lipopolysaccharide (LPS) and enables cellular response to LPS," J. Biol. Chem., 1995, 270:1382-1387.

(56) References Cited

OTHER PUBLICATIONS

Kajander et al., "Dual interaction of factor H with C3d and glycosaminoglycans in host-nonhost discrimination by complement," PNAS, 108: 2897-2902 (2011).
Kennedy et al., "A complex of soluble MD-2 and lipopolysaccharide serves as an activating ligand for Toll-like receptor 4," J. Biol. Chem., 279:34698-34704 (2004).
Kraiczy and Wurzner. "Complement escape of human pathogenic bacteria by acquisition of complement regulators," Mol Immunol, 43: 31-44 (2006).
LaBeta et al., "Release from a human monocyte-like cell line of two different soluble forms of the lipopolvsaccharide receptor, CD14," Eur. J. Immunol., 23:2144-2151 (1993).
Laga et al., "Non-ulcerative sexually transmitted diseases as risk factors for HIV-1 transmission in women: results from a cohort study [see comments]," Aids, 7: 95-102 (1993).
Laga et al., "The interrelationship of sexually transmitted diseases and HIV infection: implications for the control of both epidemics in Africa," AIDS, 5 Suppl 1: S55-63 (1991).
Lahra et al., "A new multidrug-resistant strain of Neisseria gonorrhoeae in Australia," N Engl J Med, 371: 1850-1851 (2014).
Landmann et al., "Increased circulating soluble CD14 is associated with high mortality in gramnegative septic shock," J. Infect. Dis., 171:639-644 (1995).
Latz et al., "Lipopolysaccharide rapidly traffics to and from the Golgi apparatus with the toll-like receptor 4-MD 2-CD14 complex in a process that is distinct from the initiation of signal transduction," J. Biol. Chem., 277:47834 (2002).
Latz et al., "The LPS receptor generates inflammatory signals from the cell surface," J. Endotoxin. Res., 9:375 (2003).
Latz et al., "TLR9 signals after translocating from the ER to CpG DNA in the lysosome," Nat. Immunol., 5(2):190-198 (2004).
Lawson et al., "Treatment of murine lupus with cDNA encoding IFN-)'R/Fc," J. Clin. Invest., 106:207-215 (2000).
Lawton et al., "Novel therapeutic strategies based on toll-like receptor signaling," Current Opinion in Chem Biol., 7: 446-451 (2003).
LeBouder et al., "Soluble forms of Toll-like receptor (TLR)2 capable of modulating TLR2 signaling are present in human plasma and breast milk," J. Immunol., 171(12):6680-6689 (2003).
Lewis et al., "Defining targets for complement components C4b and C3b on the pathogenic neisseriae," Infect Immun, 76: 339-350 (2008).
Lewis, "alpha-2,3-Sialyltransferase Expression Level Impacts the Kinetics of Lipooligosaccharide Sialylation, Complement Resistance, and the Ability of Neisseria gonorrhoeae to Colonize the Murine Genital Tract," MBio 6, 6: e02465-14 (2015).
Li et al., "Antimicrobial susceptibility of Neisseria gonorrhoeae isolates from symptomatic men attending the Nanjing sexually transmitted diseases clinic (2011-2012): genetic characteristics of isolates with reduced sensitivity to ceftriaxone," BMC Infect Dis, 14: 622 (2014).
Lien et al., "Toll-like receptor 4 imparts ligand-specific recognition of bacterial lipopolysaccharide," J. Clin. Invest., 105:497 (2000).
Madico et al., "Factor H Binding and Function in Sialylated Pathogenic Neisseriae is Influenced by Gonococcal, but Not Meningococcal, Porin," J Immunol, 78: 4489-4497 (2007).
Manuelian et al., "Mutations in factor H reduce binding affinity to C3b and heparin and surface attachment to endothelial cells in hemolytic uremic syndrome," J Clin Invest, 111: 1181-1190 (2003).
Martin et al., "Rapid sequence-based identification of gonococcal transmission clusters in a large metropolitan area," J Infect Dis, 189: 1497-1505 (2004).
McQuillen et al., "Complement processing and immunoglobulin binding to Neisseria gonorrhoeae determined in vitro simulates in vivo effects," J Infect Dis, 179: 124-135 (1999).
McQuillen et al., "Complement-mediated bacterial killing assays," Methods Enzymol, 236: 137-147 (1994).
Meng et al., "Antagonistic antibody prevents toll-like receptor 2-driven lethal shock-like syndromes," J. Clin. Invest., 113(10):1473-1481 (2004).
Meri et al., "Microbes bind complement inhibitor factor H via a common site," PLoS Pathog, 9: e1003308 (2013).
Mullarkey et al., "Inhibition of endotoxin response by e5564, a novel Toll-like receptor 4-directed endotoxin antagonist," J. Pharmacol. Exg. Ther., 304: 1093 (2003).
Mullen et al., "The role of disulfide bonds in the assembly and function of MD 2," PNAS, 100:3919 (2003).
Nagai et al., "Essential role of MD 2 in LPS responsiveness and TLR4 distribution," Nat. Immunol., 3: 667-672 (2002).
Navia et al., "Crystal structure of galactan-binding mouse immunoglobulin J539 Fab at 4.5-A resolution," PNAS, 76:4071-4074 (1979).
Nester et al., "Atypical aHUS: State of the art," Mol Immunol, 67: 31-42 (2015).
Ngampasutadol et al., "Human Factor H Interacts Selectively with Neisseria gonorrhoeae and Results in Species-Specific Complement Evasion," J Immunol, 180: 3426-3435 (2008).
Ohnishi et al., "Is Neisseria gonorrhoeae initiating a future era of untreatable gonorrhea?: detailed characterization of the first strain with high-level resistance to ceftriaxone," Antimicrob Agents Chemother, 55:3538-3545 (2011).
Pangburn et al., "Human complement C3b inactivator: isolation, characterization, and demonstration of an absolute requirement for the serum protein beta1H for cleavage of C3b and C4b in solution," J Exp Med, 146: 257-270 (1977).
Parsons et al., "The serum resistance of gonococci in the majority of urethral exudates is due to sialylated lipopolysaccharide seen as a surface coat," FEMS Microbial Lett, 69: 295-299 (1992).
Paul, Fundamental Immunology, 5th edition. 2003 Chapter 3 (p. 56-58): The lmmunoglobulin Hinge.
Poltorak et al., "Physical contact between lipopolysaccharide and Toll-like receptor 4 revealed by genetic complementation," PNAS, 97:2163 (2000).
Pugin et al., "Soluble MD-2 activity in plasma from patients with severe sepsis and septic shock," Blood, 104(13):4071-4079 (2004).
R&D Systems, "Recombinant Mouse CD14/Fc Chimera," Catalog No. 982-CD, 2001, 1 page.
Ram et al., "Binding of C4b-binding protein to porin: a molecular mechanism of serum resistance of Neisseria gonorrhoeae," J. Exp. Med., 193:281 (2001).
Ram et al., "C4bp binding to porin mediates stable serum resistance of Neisseria gonorrhoeae," Int. Immunophatmacol., 1:423-432 (2001).
Ram et al., "A novel sialic acid binding site on factor H mediates serum resistance of sialylated Neisseria gonorrhoeae," J Exp Med, 187: 7 43-752 (1998).
Ram et al., "Binding of complement factor H to loop 5 of porin protein IA: a molecular mechanism of serum resistance of nonsialylated Neisseria gonorrhoeae," J Exp Med, 188: 671-680 (1998).
Ray et al., "Novel blocking human IgG directed against the pentapeptide repeat motifs of Neisseria meningitidis Lip/H.8 and Laz lipoproteins," J Immunol, 186: 4881-4894 (2011).
Re et al., "Monomeric recombinant MD 2 binds TLR4 tightly and confers LPS responsiveness," L. Biol. Chem., 277: 23427-23432 (2002).
Ricklin et al., "Complement: a key system for immune surveillance and homeostasis," Nat Immunol, 11: 785-797 (2010).
Ripoche et al., "The complete amino acid sequence of human complement factor H," Biochem, J 249: 593-602 (1988).
Robinson et al., "Optimizing the stability of single-chain proteins by linker length and composition mutagenesis," PNAS, 95:5929-5934 (1998).
Rodriguez et al., "New functional and structural insights from updated mutational databases for complement factor H, Factor I, membrane cofactor protein and C3," Biosci Rep, 34: e00146 (2014).
Rossolini et al., "Update on the antibiotic resistance crisis," Curr Opin Pharmacol, I8C: 56-60 (2014).
Rothenfusser et al., "Recent advances in immunostimulatory CpG oligonucleotides," Curr. Opin. Mol. Ther., 5(2):98-106 (2003).

(56) References Cited

OTHER PUBLICATIONS

Saitoh et al., "Lipid A antagonist, lipid IVa, is distinct from lipid A in interaction with Toll-like receptor 4 (TLR4)-MD 2 and ligand-induced TLR4 oligomerization," Int. Immunol., 16:961 (2004).
Sarantis and Gray-Owen, "Defining the roles of human carcinoembryonic antigen-related cellular adhesion molecules during neutrophil responses to Neisseria gonorrhoeae," Infect Immun, 80: 345-358 (2012).
Schmidt et al., "A new map of glycosaminoglycan and C3b binding sites on factor," J Immunol, 181: 2610-2619 (2008).
Schneider et al., "Expression of paragloboside-like lipooligosaccharides may be a necessary component of gonococcal pathogenesis in men," J Exp Med, 174:1601-1605 (1991).
Schromm et al., "Molecular genetic analysis of an endotoxin nonresponder mutant cell line: a point mutation in a conserved region of MD 2 abolishes endotoxin-induced signaling," J. Exp. Med, 194:79 (2001).
Shafer et al., "Serum sensitivity of Neisseria gonorrhoeae: the role of lipopolysaccharide," J Infect Dis, 149: 175-183 (1984).
Sharma et al., "Identification of three physically and functionally distinct binding sites for C3b in human complement factor H by deletion mutagenesis," PNAS, 93: I 0996-11001 (1996).
Shaughnessy et al., "Fusion protein comprising factor H domains 6 and 7 and human IgG 1 Fe as an antibacterial immunotherapeutic," Clin Vaccine Immunol, 21: 1452-1459 (2014).
Shaughnessy et al., "Molecular characterization of the interaction between sialylated Neisseria gonorrhoeae and factor H," J Biol Chem, 286: 22235-22242 (2011).
Shimazu et al., "MD-2, a molecule that confers lipopolysaccharide responsiveness on Toll-like receptor4," J. Exp. Med., 189(11):1777-1782 (1999).
Takeuchi et al., "Cutting edge: role of Toll-like receptor 1 in mediating immune response to microbial lipoproteins," J. Immunol., 169: 10-14 (2002).
Takeuchi et al., "Discrimination of bacterial lipoproteins by Toll-like receptor 6," Int. Immunol., 13:933-940 (2001).
Triantafilou et al., "Combinational clustering of receptors following stimulation by bacterial products determines lipopolysaccharide responses," Biochem. J., 381:527 (2004).
Ulevitch et al., "Recognition of Gram-negative bacteria and endotoxin by the innate immune system," Curr. Opin. In Immn., 11: 19-22 (1999).
Unemo and Shafer, "Antimicrobial resistance in Neisseria gonorrhoeae in the 21st century: past, evolution, and future," Clin Microbiol Rev, 27: 587-613 (2014).
Viriyakosol and Kirkland, "The N-terminal half of membrane CD14 is a functional cellular lipopolysaccharide receptor," Infect. Immun., 64(2):653-656 (1996).
Visintin et al., "Lysines 128 and 132 enable lipopolysaccharide binding to MD-2, leading to Toll-like receptor-4 aggregation and signal transduction," J. Biol. Chem., 278(48):48313-48320 (2003).
Visintin et al., "Secreted MD 2 is a large polymeric protein that efficiently confers lipopolysaccharide sensitivity to Toll-like receptor 4," PNAS, 98: 12156-61 (2001).
Visintin et al., "Pharmacological inhibition of endotoxin responses is achieved by targeting the TLR4 coreceptor, MD-2," J Immunol, 175: 6465-6472 (2005).
Walker et al., "Environment. Looming global-scale failures and missing institutions," Science, 325: 1345-1346 (2009).
Weber et al., "Binding of the *Drosophila* cytokine Spatzle to Toll is direct and establishes signaling," Nat. Immunol., 4:794 (2003).
Weiler et al., "Control of the amplification convertase of complement by the plasma protein beta1H," PNAS, 73: 3268-3272 (1976).
Whaley and Ruddy, "Modulation of the alternative complement pathways by beta 1 H globulin," J Exp Med, 144: 1147-1163 (1976).
WHO, "Global action plan to control the spread and impact of antimicrobial resistance in Neisseria gonorrhoeae," World Health Organization (WHO), Department of Reproductive Health and Research, 40 pages (2012).
Wu and Jerse, "Alpha-2,3-sialyltransferase enhances Neisseria gonorrhoeae survival during experimental murine genital tract infection," Infect Immun, 74: 4094-4103 (2006).
Wu et al., "Relative importance of LOS sialylation and the MtrC-MtrD-MtrE active efflux pump in gonococcal evasion of host innate defenses," In XVIIIth International Pathogenic Neisseria Conference, Wuerzburg, Germany, 364 (2012).
Wurzner, "Evasion of pathogens by avoiding recognition or eradication by complement, in part via molecular mimicry," Mal Immunal, 36: 249-260 (1999).
Yang et al., "Variation of gonococcal lipooligosaccharide structure is due to alterations in poly-G tracts in lgt genes encoding glycosyl transferases," J Exp Med, 183: 323-327 (1996).

* cited by examiner

FACTOR H-FC IMMUNOTHERAPHY

CLAIM OF PRIORITY

This application is a national phase under 35 U.S.C. § 371 of PCT International Application No. PCT/US2016/059072, filed on Oct. 27, 2016, which claims the benefit of U.S. Provisional Patent Application Ser. No. 62/246,662, filed on Oct. 27, 2015. The entire contents of each of the foregoing applications are hereby incorporated by reference.

FEDERALLY SPONSORED RESEARCH OR DEVELOPMENT

This invention was made with Government support under Grant Nos. AI111728, AI118161, AI054544 and AI032725 awarded by the National Institutes of Health. The Government has certain rights in the invention.

TECHNICAL FIELD

Described herein are fusion proteins comprising Factor H (FH) domains 18-20 (FH18-20) linked via an optional linker to IgG Fc, wherein the FH has mutation of D to G at position 1119 in domain 19; FHD1119G/Fc), and methods of use thereof, e.g., to treat pathogen infections.

BACKGROUND

Antimicrobial resistance remains a major threat to public health worldwide and we are witnessing an era where several medically important microbes are becoming untreatable with antibiotics currently in clinical use. Organisms such as *Staphylococcus aureus, Enterococcus* spp, *Pseudomonas aeruginosa, Acinetobacter baumanii*, and several additional members of the family Enterobacteriaceae have become resistant to most conventional antibiotics (1, 2). Similarly, *Neisseria gonorrhoeae* has also demonstrated a remarkable capacity to resist almost every antibiotic that it has encountered (3). The recent isolation of *N. gonorrhoeae* strains resistant to ceftriaxone, the last remaining option for empirical monotherapy, in several parts of the world represents a major public health problem (4-7). In addition to complications including pelvic inflammatory disease and its sequelae such as infertility, ectopic pregnancy and chronic pelvic pain, gonorrhea can increase the transmission and acquisition of HIV-1 infection (8, 9). Thus, spread of multidrug resistant gonorrhea represents a serious public health threat and there is an urgent need to develop novel antimicrobials and (ideally) vaccines and immunotherapeutics against this pathogen.

SUMMARY

*Neisseria gonorrhoeae* (Ng), the causative agent of the sexually transmitted infection gonorrhea, has developed resistance to almost every conventional antibiotic. There is an urgent need to develop novel therapies against gonorrhea. Many pathogens, including Ng, bind the complement inhibitor factor H (FH) to evade complement-dependent killing. Chimeric proteins comprising human FH domains 18, 19 and 20 fused to murine IgG2a Fc (FH18-20/Fc) bound to gonococci, activated the classical pathway of complement, and resulted in complement-dependent bactericidal activity (27). Such a molecule could serve as a novel adjunctive immunotherapeutic against multidrug-resistant bacterial species, including *N. gonorrhoeae*. However, the C-terminus of FH is also critical for regulating complement activation on host cells (28,29). Therefore, a therapeutic that uses the C-terminus of FH to anchor complement-activating Fc to the bacterial surface needs to be modified to eliminate binding to host cells.

Sialylation of gonococcal lipooligosaccharide (LOS), as occurs in vivo, augments binding of human FH through its domains 18-20 (FH18-20). We explored the utility of fusing FH18-20 with IgG Fc (FH18-20/Fc) to create a novel anti-infective immunotherapeutic. FH18-20 also binds to select host glycosaminoglycans to limit unwanted complement activation on host cells. To identify mutation(s) in FH18-20 that eliminated complement activation on host cells, yet maintained binding to Ng, we created four mutations in domains 19 or 20 described in atypical hemolytic uremic syndrome that prevented binding of mutated fH to human erythrocytes. One of the mutant proteins (D to G at position 1119 in domain 19; FHD1119G/Fc) facilitated complement-dependent killing of gonococci similar to unmodified FH18-20/Fc, but unlike FH18-20/Fc, did not lyse human erythrocytes. FHD1119G/Fc bound to all (100%) of 15 sialylated clinical Ng isolates tested (including three contemporary ceftriaxone-resistant strains), mediated complement-dependent killing of 10/15 (67%) strains and enhanced C3 deposition (>10-fold above baseline levels) on each of the five isolates not directly killed by complement. FHD1119G/Fc facilitated opsonophagocytic killing of a serum-resistant strain by human polymorphonuclear neutrophils. FHD1119G/Fc administered intravaginally significantly reduced the duration and burden of gonococcal infection in the mouse vaginal colonization model. FHD1119G/Fc represents a novel immunotherapeutic against multidrug-resistant Ng.

Thus, in a first aspect the invention provides polypeptides comprising Factor H (FH) domains 18-20 (FH18-20) linked via an optional linker to IgG Fc, wherein the FH18-20 has mutation at position 1119 in domain 19, and wherein the linker comprises at least two additional amino acids between the FH domain and the Fc region.

In some embodiments, the Fc region is derived from a human immunoglobulin or a murine immunoglobulin.

In some embodiments, the linker comprises at least one glycine or one alanine. In some embodiments, the linker comprises GAAGG (SEQ ID NO:1) or AAAGG (SEQ ID NO:2).

In some embodiments, the polypeptide further comprises a peptide tag, e.g., hemagglutinin (HA), FLAG, HIS, c-Myc, VSV-G, V5, or HSV.

In some embodiments, the FH18-20 has a mutation of D to G at position 1119 in domain 19.

Also provided herein are pharmaceutical compositions comprising fusion proteins described herein, and a pharmaceutically acceptable carrier, e.g., for use in the treatment of a disorder associated with a Factor H-binding pathogen.

Further, provided herein is the use of a fusion protein described herein in the manufacture of a medicament for the treatment of a disorder associated with a Factor H-binding pathogen. In addition, described herein are methods for treating disorders associated with a Factor H-binding pathogen in a subject, the method comprising administering a therapeutically effective amount of a fusion protein described herein.

In some embodiments, the disorder is infection with *N. gonorrhoeae*, and the methods include administering a therapeutically effective amount of a fusion protein as described herein.

In some embodiments, the disorder is a pathogen-associated infection.

In some embodiments, the pathogen is selected from the group consisting of bacteria, fungi, viruses, spirochetes, and parasites.

In some embodiments, the bacterium is selected from the group consisting of *P. aeruginosa, S. pneumoniae, Y. pestis, E. coli, S. typhimurium, N. meningitidis, N. gonorrhoeae, H. influenza* and *S. aureus*.

In some embodiments, the fungus is selected from the group consisting of *Aspergillus fumigatus, Candida albicans*, and other zymosan-containing fungi.

In some embodiments, the spirochete is *Borrelia burgdorferi* or *Treponema pallidum*.

In some embodiments, the parasite is *Plasmodium berghei* or *Plasmodium falciparum*.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
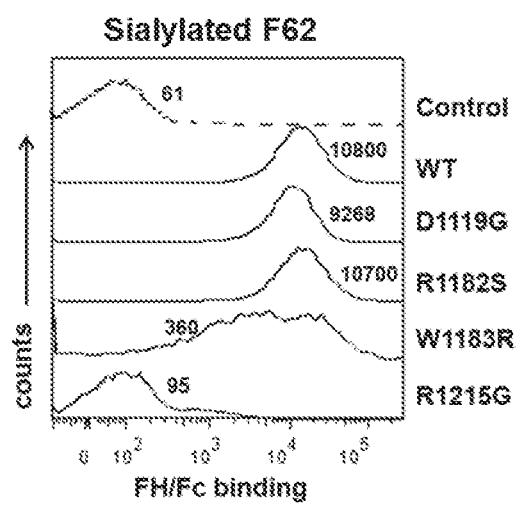
FIGS. 1A-C. Binding to, and bactericidal activity against *N. gonorrhoeae* of wild-type FH18-20/murine IgG2a Fc and its derivatives containing point mutations in the FH region. A. Binding of WT FH18-20/murine IgG2a Fc and mutant proteins to *N. gonorrhoeae* strain F62 grown in media containing CMP-Neu5Ac (2 µg/ml) to sialylate its LOS. The D1119G mutation is located in FH domain 19; R1182S, W1183R and R1215G mutations are in FH domain 20. Each FH/Fc protein (10 µg/ml) was incubated with sialylated strain F62 and bound FH/Fc was detected by flow cytometry. Numbers alongside each histogram represents the median fluorescence of the entire bacterial population. The control reaction mixture lacks FH/Fc. B. Bactericidal activity of FH18-20/murine IgG2a Fc and mutant proteins directed against sialylated *N. gonorrhoeae*. Sialylated strain F62 (left graph) or sialylated strain 252 (right graph) were incubated with varying concentrations of each FH/Fc molecule (X-axis), followed by the addition of human complement (IgG/IgM depleted human serum [see Methods]). C. Survival of bacteria at 30 min relative to bacterial counts at the beginning of the assay (to min) is shown on the Y-axis (mean±SD of at least 2 independently performed experiments).

Resistance of pathogens to many of the currently available antimicrobial agents poses a major threat to human health worldwide. The Centers for Disease Control and Prevention (CDC) has proclaimed that N. gonorrhoeae is one of three organisms (together with Clostridium difficile and carbapenem-resistant Enterobacteriaceae) where resistance to antimicrobials represents an "urgent threat" to human health (5). The "Global action plan to control the spread and impact of antimicrobial resistance in Neisseria gonorrhoeae" recently published by the WHO emphasizes the need for novel approaches to prevent and treat gonorrhea (54). Newer modalities of treatment whose mechanism(s) of action differ from those of conventional agents provide hope that drug-resistance may be deterred when traditional mechanisms of selection are circumvented (3).

The complement system forms a key arm of innate immune defenses against invading pathogens (10). In order to successfully establish infections in their hosts, microbes have developed mechanisms to subvert killing by complement (11). By binding of complement inhibitors, such as factor H (FH), C4b-binding protein (C4BP) and vitronectin, several pathogens, including N. gonorrhoeae, dampen complement activation on their surfaces (11-13). FH inhibits the alternative pathway of complement by serving as a cofactor for the factor I-mediated cleavage of C3b to the hemolytically inactive iC3b fragment (14). FH also possesses decay accelerating activity, whereby it irreversibly dissociates the Bb fragment from the alternative pathway C3 convertase, C3b,Bb (15-17). FH comprises 20 domains, also known as short consensus repeat domains (SCRs) or complement control protein domains (CCPs) that are arranged in the form of a single chain (18). The first four N-terminal domains are necessary and sufficient for complement inhibition (19). Most microbes, including N. gonorrhoeae, that bind FH do so through regions spanned by domains 6 and 7 and/or domains 18 through 20 (11).

Sialylation of gonococcal LOS is an important component of gonococcal pathogenesis, which occurs in humans (20, 21) and also during experimental infection of mice (55). In vivo, gonococci scavenge 5'-cytidinemonophospho-N-acetylneuraminic acid (CMP-Neu5Ac) from the host to sialylate their lipooligosaccharide (LOS) (20, 21). The two LOS structures that can be sialylated are the nearly ubiquitously expressed lacto-N-neotetraose (LNT, Neu5Acα2-3Galβ1-4GlcNAcβ1-3Galβ1-4Glcβ1-4HepI) structure and the less frequently encountered $P^k$-like structure (Neu5Acα2-6Galα1-4Galβ1-4Glcβ1-4HepI) (22). Sialylation of the LNT LOS structure enhances binding of the C-terminal domains 18-20 of human FH to gonococci (23, 24). This increase in FH binding is dependent on expression of gonococcal porin (PorB); replacing gonococcal PorB with meningococcal PorB abrogates Neu5Ac-mediated enhancement of FH binding (25). Several strains of N. gonorrhoeae also bind FH independently of LOS sialylation (26). Gonococcal mutants that are incapable of LOS sialylation following deletion of the LOS sialyltransferase (1st) gene are less virulent in the mouse model of vaginal colonization (55). Sialylation of LOS facilitates evasion of gonococcal killing by the alternative and classical pathways of complement and may also augment bacterial resistance to killing by cationic peptides (56).

Figure 2:
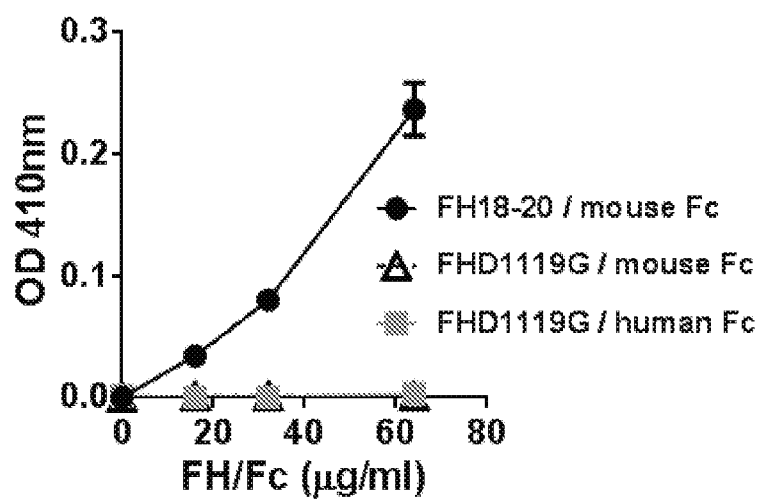
FIG. 2. Complement-mediated lysis of anti-CD59 treated RBCs by FH/Fc fusion proteins. Increasing concentrations (indicated on the X-axis) of wild type FH18-20/murine IgG2a Fc or FHD1119G/Fc (either murine IgG2a Fc or human IgG1 Fc) were added to anti-CD59-treated human RBCs in GVB/Mg$^{++}$EGTA followed by the addition of homologous NHS to a concentration of 40%. The reaction mixture was then incubated at 37° C. for 20 min. Cold GVB/EDTA was added, samples were centrifuged and $OD_{410\ nm}$ was measured to determine degree of hemolysis (indicated on the Y-axis). Each experiment was performed in duplicate and results indicated and each point represents the mean (SD).

LOS sialylation enhances FH binding through C-terminal domains of FH (24, 27). In addition, a chimeric molecule comprising FH domains 18-20 fused to mouse IgG2a Fc mediates complement-dependent killing of sialylated gonococci (27). Killing of gonococci by FH/Fc is classical pathway dependent and occurs at Fc concentrations well below that required to block FH binding to bacteria (27). However, because the C-terminal domains of FH plays a key role in "self-nonself" discrimination (28, 29), the use of a FH18-20/Fc molecule with an unmodified FH has the capacity to bind to human cells and activate complement; this is revealed in our experiments of complement-dependent lysis of anti-CD59-treated RBCs by unmodified FH18-20/Fc (FIG. 2). FH domains 19 and 20 interact with C3 fragments and glycosaminoglycans respectively, to limit complement activation on host cells (28, 29), Therefore it was necessary to introduce a mutation in the FH fragment to abrogate toxicity. To achieve this, we capitalized on prior work that characterized select mutations in FH domains 19 and 20 that have been described in individuals with aHUS (37). We focused on four FH mutations that did not interfere with full-length FH's inhibition of lysis of human erythrocytes and selected a mutant, FHD1119G/Fc that showed activity that was comparable to FH18-20/Fc activity against gonococci but did not exhibit complement-dependent lysis of human RBCs.

Figure 5:
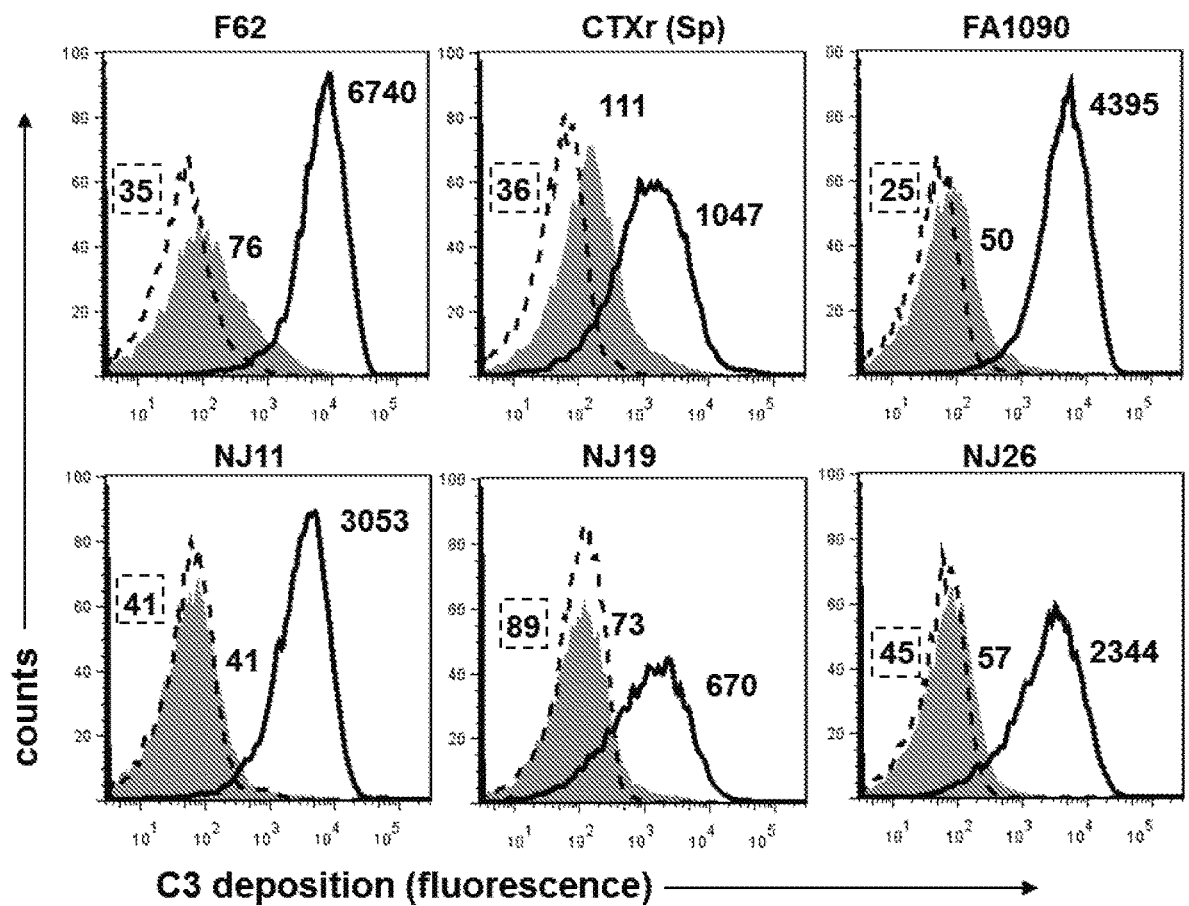
FIG. 5. C3 fragment deposition on 5 sialylated strains that resisted killing by complement: FA1090, CTXr (Spain); NJ-11; NJ-19 and NJ-26 (indicated by "#" in FIG. 4). Sialylated strains were incubated with FHD1119G/human IgG1 Fc (33.3 µg/ml) and 20% (v/v) human complement. Sialylated F62 served as a positive control. C3 fragments (C3b/iC3b) deposited on bacteria in the presence of FHD1119G/Fc were detected by flow cytometry (histograms shown with a solid black line). C3 fragment deposition on bacteria incubated with complement alone shown by the grey shaded histogram and antibody conjugate controls (bacteria plus anti-C3c FITC) by the dashed histogram. The number next to each histogram represents median fluorescence. One representative experiment of two reproducible repeat experiments is shown.
Figure 6:
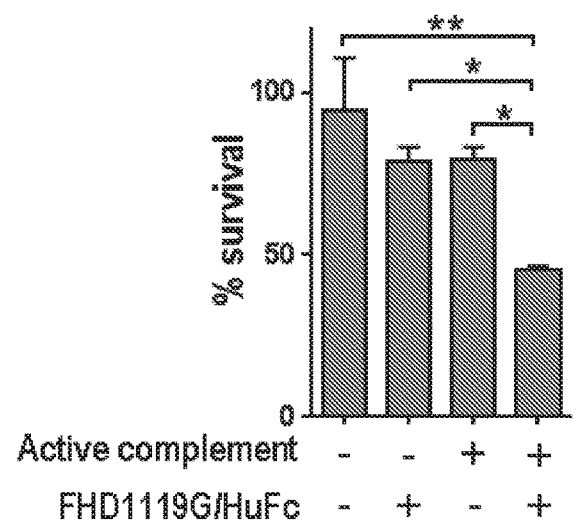
FIG. 6. Opsonophagocytic killing of the sialylated Opa-negative mutant of *N. gonorrhoeae* FA1090 by FHD1119G/human Fc and complement. Opa-negative FA1090 grown in media containing CMP-Neu5Ac to sialylate lipooligosaccharide (LOS)($10^7$ CFU) was incubated with FHD1119G/human Fc (FHD1119G/HuFc; 16.7 µg/ml) and 20% (v/v) human complement, followed by the addition of $10^6$ freshly isolated human PMNs for 60 min at 37° C. (MOI 10:1). Bacterial survival at 60 min relative to to is shown on the Y-axis (mean [SD] of 4 independently performed experiments). Controls included reactions where complement was heat-inactivated (indicated by "-" in the "Active complement" row), or where FHD1119G/Fc was omitted. *, P<0.05; **, P<0.01 (ANOVA).

It is worth noting that although FHD1119G/Fc did not cause direct complement-mediated killing of five of 15 tested isolates (FIG. 4), it enhanced C3 deposition on all of these five isolates (FIG. 5) and resulted in opsonophagocytic killing of an Opa-negative mutant derived from one of these strains (FIG. 6). The reason(s) for the resistance of these five strains to direct complement-dependent killing despite the observed enhanced C3 deposition is not clear. Possible (and not mutually exclusive) explanations include insufficient C5 convertase formation and/or prevention of effective C5b-9 formation, for example by binding vitronectin (57-60). The relative roles of membrane attack complex-mediated bacterial killing versus opsonophagocytosis in clearance of gonococci in vivo remains to be elucidated.

FHD1119G/Fc showed activity against gonococci in the mouse vaginal colonization model and represents a promising initial step in the search for novel therapeutics against gonorrhea that is rapidly becoming multidrug-resistant. We acknowledge that further studies to evaluate the safety of FH/Fc as well as its efficacy against other strains of gonorrhea are needed.

Notably, Meri et al (61) showed that the D1119G mutation in FH domain 19 did not affect binding to several microbes, including *Pseudomonas aeruginosa, Haemophilus influenzae, Bordetella pertussis, Streptococcus pneumoniae* and *Candida albicans*, suggesting that FHD1119G/Fc may also enhance complement activation and possess therapeutic activity against these pathogens. In particular, *P. aeruginosa* and *C. albicans* have been cited by the CDC as microbes where drug-resistance represents a "serious" threat level (5). Activity of FHD1119G/Fc as an adjunctive treatment in these infections merits study.

In this study we have focused on LOS sialylation, a key virulence mechanism of gonococci, to design a novel FH/Fc fusion protein that possesses bactericidal activity (either direct killing by complement or through opsonophagocytosis) against a wide array of gonococcal isolates in vitro. In order to develop resistance to this agent, gonococci would have to lose the ability to sialylate LOS and bind to FH; decrease in resistance to complement and cationic peptides would result in diminished fitness and pose a barrier to the development of drug-resistance, which may not be simply overcome by the traditional microbial mechanism of "escape mutation" (3). Accordingly, gonococci that lack the ability to sialylate its LOS (1st deletion mutant) are out-competed by the parent strain in the mouse vaginal colonization model (55, 62).

Here we describe derivation of a novel fully human FH18-20/Fc fusion immunotherapeutic molecule (FHD1119G/Fc) that shows activity both in vivo and in vitro against diverse *N. gonorrhoeae* isolates, and which may also be active against *Pseudomonas aeruginosa, Haemophilus influenzae, Bordetella pertussis, Streptococcus pneumoniae* and *Candida albicans*, among other pathogens.

Factor H

Factor H is a complement-inhibitory molecule whose main roles are to limit the amount of C3b deposited on a surface and also facilitate the conversion of active C3b to the hemolytically inactive molecule, iC3b, and thus limit complement activation that prevents activation of the lytic effector system. The binding of Factor H to the surface of some bacteria confer them a "protective" effect against the C-dependent lysis. Factor H pathogen recognition molecules can be derived from, e.g., *Homo sapiens* (GeneID: 3075; UniGene Hs.363396; NCBI Accession #NP_000177.2 or P08603). In some embodiments, the Factor H PRM includes CCP/Sushi domains 18-20 described in Table A; the numbers refer to the amino acids of NCBI Accession #NP_000177.2.

TABLE A

| CCP/Sushi domains 18-20 of human complement factor H | | |
|---|---|---|
| CCP/Sushi 18 | 1046 | 1104 |
| CCP/Sushi 19 | 1107 | 1165 |
| CCP/Sushi 20 | 1170 | 1230 |

The Factor H domains used in the fusion proteins described herein include at least one mutation, a mutation of D at position 1119 in domain 19, referred to herein as FH(18-19)D1119X. In some embodiments, the mutation is a D to G mutation, although other amino acids can also be substituted for the D (referred to herein as FH(18-19) D1119G), e.g., Alanine (A), isoleucine (I), Leucine (L), Proline (P), or Serine (S).

In some embodiments, the FH(18-19)D1119X comprises SEQ ID NO:3; the position 1119 is shown here as a bold, double underlined "X":

```
                                        (SEQ ID NO: 3)
CVNPPTVQNAYIVSRQMSKYPSGERVRYQCRSPYEMFGDEEVIVICLNGN

WTEPPQCKDSTGKCGPPPPIDNGXITSFPLSVYAPASSVEYQCQNLYQLE

GNKRITCRNGQWSEPPKCLHPCVISREIMENYNIALRWTAKQKLYSRTGE

SVEFVCKRGYRLSSRSHTLRTTCWDGKLEYPTCAKR
```

Fc Modules

The mouse and human immunoglobulin (IgG) heavy chain has four Ig-like domains termed $V_H$ (Variable heavy) and $C_{H1}$ (Constant heavy 1) to $C_{H3}$ (Constant heavy 3). A "hinge" region separates the $C_{H1}$ and $C_{H2}$ domains. The hinge region contains a variable number of cysteine residues (three in the mouse $IgG_{2a}$) that can form covalent interchain bonds between two identical immunoglobulin heavy chains. The portion of an immunoglobulin comprising the hinge region plus the domains $C_{H2}$ and $C_{H3}$ is called fragment crystallizable (Fc). There are several different human and other mammalian (e.g., murine) IgG molecules. For example, the human equivalent of mouse IgG2a is the IgG1. Several immunotherapeutic agents for human therapy include the human IgG1 Fc portion. A portion of the Fc molecules is used to prepare the Fc portion of the chimeric fusion protein molecules described herein.

The fusion proteins can contain sequences from the same species or from different species. For example, an interspecies hybrid fusion protein can contain a murine Fc region and a human sequence from an FH protein. The fusion proteins described herein also preferably fully human (i.e., a human FH 18-20 domain and a human Fc region). In general, both the FH module and the Fc region of a fusion protein for use in a specific animal species are derived from that animal species. Thus, a human FH(18-20):human Fc fusion protein is generally used in humans.

General methods of preparing fusion proteins are known in the art (Ashkenazi, A. and S. M. Chamow (1997), "Fusion proteins as research tools and therapeutic agents," Curr. Opin. Immunol. 9(2): 195-200, Chamow, S. M. and A. Ashkenazi (1996). "Fusion proteins: principles and applications," Trends Biotechnol. 14(2):52-60). In general, to generate a fusion protein, the sequences encoding the hinge region of an Ig are retained and a region coding for a short (e.g., about 5 amino acid) linker is added between the pathogen recognition module coding region and the region coding for the Fc (n-terminal to the hinge). The main effector region of the Fc (i.e., the region that binds complement and protein A, and the single glycosylation site that is required to stabilize an Fc dimer—the effector functions are C-terminal to the hinge region) should be included.

In one example, a fusion protein can be made by cloning into an expression vector such as pcDNA3 (Invitrogen) a nucleic acid sequence encoding a TLR ECD in-frame with a sequence encoding an Fc portion of an Ig (e.g., the Fc portion of an IgG such as an IgG2a).

In one embodiment, the Fc portion and a linker (in bold print below) has the murine sequence:

(SEQ ID NO: 4)
AAAGGEPRGPTIKPCPPCKCPAPNLLGGPSVFIFPPKIKDVLMISLSPIV

TCVVVDVSEDDPDVQISWFVNNVEVHTAQTQTHREDYNSTLRVVSALPIQ

HQDWMSGKEFKCKVNNKDLPAPIERTISKPKGSVRAPQVYVLPPPEEEMT

KKQVTLTCMVTDFMPEDIYVEWTNNGKTELNYKNTEPVLDSDGSYFMYSK

LRVEKKNWVERNSYSCSVVHEGLHNHHTTKSFSRTPGK.

In other embodiments, the Fc portion can be derived from the human Ig gamma-1 chain C region (Swiss-Prot Accession No. P01857), in which the hinge starts from residue 99:

(SEQ ID NO: 5)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLEPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSR[D/E]E[L/M]T

KNQVSLTCLVKGFYPSDIAVEWESNGQPENNYKTTPPVLDSDGSFFLYSK

LTVDKSRWQQGNVFSCSVMHEALHNHYTQKSLSLSPGK.

In some embodiments, the Human IgG1 sequence used is:

(SEQ ID NO: 6)
EPKSCDKTHTCPPCPAPELLGGPSVFLEPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGK

Linkers

In some embodiments, the fusion protein construct includes a linker, e.g., in the form of additional residues, e.g., alanine and/or glycine residues, between the FH(18-20) and the Fc/Ig hinge region. The total number of linker residues (in addition to glycine residues that are naturally occurring in the Ig from which the hinge region is derived) can be, e.g., at least 2, 3, 4, 5, 6, or 7. To minimize the possibility of immunological rejection of the molecule and retain expression and proper folding other residues can be used. These include naturally occurring Ig hinge regions or part of non-structured regions of human extracellular proteins. As a general rule, when designing a Fusion protein hinge region, peptide sequences including small, slightly hydrophilic amino acids such as glycine, alanine, serine, threonine, methionine are preferred over charged, ring or aromatic residues. Thus, the total number of resides, e.g., alanine and/or glycine residues in the linker region can be, e.g., at least 2, 3, 4, 5, 6, 7, 8, or 9. Examples of linkers include GAAGG (SEQ ID NO:1) and AAAGG (SEQ ID NO:2). These examples are not to be construed as limiting and in general, a linker that results in a fusion protein that can bind to its cognate ligand is encompassed by the invention. In some embodiments, the nucleic acid sequence that encodes the linker includes a restriction enzyme recognition site, e.g., Not I, to facilitate generation of fusion protein constructs.

Fusion Proteins

The methods and compositions described herein can be used to make fusion proteins that are highly purified. Such highly purified proteins can be used, e.g., in a method of treating a subject who has an infection.

Constructs encoding fusion proteins can be transfected into a cell using methods known in the art. The cells can be cultured under conditions suitable for expression of the cloned fusion protein. Suitable cells include HEK293 (human), COS7 (monkey), and CHO (hamster) cells, although for production purposes, any eukaryotic cell type that can be engineered to produce a correctly folded and glycosylated fusion protein of interest can be used, including insect expression systems. In general, cells that produce antibodies (e.g., B cells) are not used.

The fusion protein vector or construct (a vector that encodes a fusion protein) can be further engineered such that a secretory signal is part of the fusion protein. Methods are known in the art for engineering a nucleic acid sequence to encode a secretory signal such that a fusion protein is secreted or embedded in the membrane. An inducible promoter can also be positioned to control the expression of the fusion protein so that expression of the fusion protein can be induced. Examples of such inducible promoters include a metallothionein promoter, a tetracycline sensitive promoter (tet- on tet-off), or a copper-inducible promoter. In addition, a fusion protein vector can have a retroviral backbone and/or include a gene that confers antibiotic resistance to a cell. Thus, transfected or transduced cells can be selected using the antibiotic to which the gene encodes a resistance protein to select for a stable transgene.

Fusion proteins can be detectably labeled for various uses such as those described herein. Labeled fusion proteins (such as fusion proteins) can be used, for example, as commercially produced reagents for use in Factor H assays and in methods for identifying compounds that bind to Factor H.

Examples of detectable labels include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include biotin; examples of suitable fluorescent materials include umbelliferone, fluorescein, fluorescein isothiocyanate (FITC), rhodamine, dichlorotriazinylamine fluorescein, dansyl chloride or phycoerythrin (PE); examples of bioluminescent materials include luciferase (which oxidates luciferin or luminol, producing light as a byproduct), luciferin, luminol and aequorin, and examples of suitable radioactive material include $^{125}$I, $^{131}$I, $^{35}$S, $^{32}$P, $^{3}$H. Methods of linking such molecules to a polypeptide are known in the art.

In some embodiments, a fusion protein is labeled by including an additional moiety such as a FLAG epitope in the hybrid protein (e.g., by engineering a vector that encodes desired fusion protein-FLAG hybrid protein), a fluorescent protein like the green fluorescent protein and its spectrum variants, or by coupling (e.g., covalently linking) a detectable moiety such as a fluorescent molecule to the fusion protein.

Assays for Fusion Protein Activity

The fusion proteins described herein have one or more of the following activities: (1) inhibit bacterial proliferation, (2) trigger complement-mediated cytotoxicity, and/or (3) function as an artificial opsonin. For example, some fusion proteins might bind to and kill bacteria, but not activate complement deposition; other fusion proteins might enhance phagocytosis, but not activate complement, and vice-versa. Methods are described herein that can be used, e.g., to evaluate a fusion protein to measure the efficiency with which the fusion protein neutralizes the pathogens to which it binds, e.g., by these three modes of action.

In some embodiments, the methods described herein include applying a fusion protein to a test sample including a cell or living tissue or organ, and evaluating one or more activities of the fusion protein, e.g., the ability of the fusion protein to bind and/or activate complement, and/or to bind a pathogen and trigger opsonophagocytosis.

In some embodiments, the test sample is, or is derived from (e.g., a sample originally taken from) an in vivo model of a disorder as described herein. For example, an animal model, e.g., a rodent such as a rat, that is infected with a pathogen can be used, and the ability of the fusion protein to improve one or more symptoms of the disorder, e.g., clinically relevant symptoms, is evaluated.

Methods for evaluating each of these effects are known in the art; some are described herein.

A test compound that has been screened by a method described herein and determined to be active, e.g., to bind and activate complement, and/or to bind a pathogen and trigger opsonophagocytosis, can be considered a candidate compound. A candidate compound that has been screened, e.g., in an in vivo model of a disorder, e.g., an animal infected with a pathogen, e.g., a microbe, and determined to have a desirable effect on the disorder, e.g., on one or more symptoms of the disorder, can be considered a candidate therapeutic agent. Candidate therapeutic agents, once screened in a clinical setting and found to be effective, are therapeutic agents. Candidate compounds, candidate therapeutic agents, and therapeutic agents can be optionally optimized and/or derivatized, and formulated with physiologically acceptable excipients to form pharmaceutical compositions.

Opsonophagocytosis Assays

Phagocytosis is an important mechanism of bacteria killing and clearance from the site of infection. Fusion proteins might play an important role as opsonins in addition to their direct role in activating complement. Fusion proteins are chimeric proteins that contain the immunoglobulin Fc domain and preliminary studies demonstrated that they can bind Fc receptors on macrophages. When fusion proteins coat bacteria, they will likely provide anchorage sites to the Fc receptors on the surface of phagocytes and promote the Fc receptor-mediated phagocytosis of the bacterial particles. These internalized fusion protein-coated particles would be decomposed intracellularly and the components would be directed to the antigen "presentation" machinery. In addition, shed fusion protein ligands might directly enter the presentation pathways via Fc receptor internalization, thus enhancing their presentation. Either outcome would be of pivotal importance for the healing process and the establishment of an immune memory.

Fusion protein-mediated opsonization might trigger bacterial killing via MAC (membrane attack complex) deposition on their cell walls, while promoting phagocytosis and cell mediated killing by professional phagocytes. The efficiency of fusion proteins as artificial opsonins can be measured by evaluating enhanced opsonophagocytosis and antigen internalization in vitro. For example, two mechanisms of bacterial entry into cells in vitro can be evaluated: 1) uptake by "non-professional" phagocytes such as the HEK293 human embryonic kidney cell line and 2) uptake by the macrophage-like cell lines THP-1 and RAW and by human macrophages. With "non-professional" phagocytes such as HEK293 cells, bacterial binding to cells that have been transfected with different fluorescence-tagged Fc receptors can be visually followed.

We have established stably transduced cell lines expressing CD36 tagged with yellow fluorescence protein (YFP) or CD16 tagged with cyan fluorescence protein (CFP). Both receptors can be visualized in living cells by confocal microscopy, e.g., using an inverted confocal microscope equipped with four laser beams (including a pulse laser for FLIM analysis) and a warmed stage. Confocal microscopy can be used to follow the formation of Fc receptor clusters around fusion protein-treated bacteria. The experiments can be conducted under protein-free conditions to minimize interference from serum components. Bacteria are expected to bind specifically to the Fc receptors only when they are coated with the Fc-containing fusion proteins. With fusion protein bridging via their Fc portion, a fluorescent "cup" will form at the interface bacteria/cell membrane. HEK293 cells, which do not normally internalize bacteria, also might become internalization competent.

To establish whether fusion proteins can enhance phagocytosis in professional phagocytes, similar experiments can be performed, e.g., with macrophage-like cell lines such as THP-1 and RAW, and with human macrophages purified from the blood of healthy donors. Cellular internalization of bacteria that have been coated with fusion protein can be measured, with uncoated bacteria serving as controls. Commercially available Fc receptor-blocking antibodies can be used to determine the contribution of fusion protein opsonization. It is expected that under protein-free conditions, non-professional phagocytes will efficiently internalize bacteria only if they are coated with fusion protein, whereas professional phagocytes will internalize both coated and uncoated bacteria but fusion protein coating will accelerate or enhance bacterial uptake. Bacterial internalization can be measured, e.g., quantitatively by flow cytometry of cells that have been with incubated with fluorescence-tagged bacteria.

Cell mediated killing can be measured by harvesting the cells used for the phagocytosis assay (or by lysing them directly on plastic after washing or killing the non adherent bacteria with antibiotics) and determining the number of colony forming units of bacteria from the lysates.

Animal Models

Also included herein are methods of screening compounds by administering a fusion protein to an animal model of a pathogen-associated disorder. Suitable animal models are known in the art, e.g., mammals, such as mice, rats, or monkeys, infected with a microbe such as *Neisseria gonorrhoeae, Pseudomonas aeruginosa, Haemophilus influenzae, Bordetella pertussis, Streptococcus pneumonia* or *Candida albicans*.

The methods include administering at least one dose of a fusion protein to the animal model, and monitoring the animal for an effect of the compound on the disorder in the animal, e.g., an effect on a clinically relevant parameter, e.g., a parameter that is related to a clinical symptom of the disease as described herein. Methods for selecting, evaluating and scoring such parameters are known in the art.

The animal can be monitored for a change in the disorder, e.g., for an improvement in a parameter of the disorder, e.g., a parameter related to clinical outcome. In some embodiments, the parameter is fever (a trend towards or a return to normal, e.g., a decrease, would be an improvement); blood pressure (a return to normal, e.g., an increase, would be an improvement); heart rate (a trend towards or a return to normal, e.g., a decrease, would be an improvement); and respiration rate (a trend towards or a return to normal, e.g., a decrease, would be an improvement); levels of white blood cells (a trend towards or a return to normal would be an improvement); the level of oxygen (a trend towards or a return to normal, e.g., an increase, would be an improvement); the number of platelets (a trend towards or a return to normal, e.g., an increase, would be an improvement); lactic acid levels (a trend towards or a return to normal, e.g., a decrease, would be an improvement); and levels of metabolic waste products (a trend towards or a return to normal, e.g., a decrease, would be an improvement).

Pharmaceutical Compositions

A fusion protein can be incorporated into a pharmaceutical composition. Such compositions typically include the fusion protein and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include oral or parenteral, e.g., intravenous, intradermal, subcutaneous, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, e.g., tromethamine; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate, and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Such compositions can also be compounded to minimize exposure to gastric enzymes or to facilitate uptake by the intestinal tract.

For administration by inhalation, the compounds can be delivered in the form of an aerosol spray, e.g., from a pressurized container or dispenser that contains a suitable propellant, e.g., a gas such as carbon dioxide, or a nebulizer. Metered dose inhalers are known in the art and can be used. The administration by inhalation can also be used to treat more than one individual at a time, e.g., to treat an area or a number of people exposed to a pathogen.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents and liposomes. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery. Such preparations are particularly useful for treating conditions associated with pathogen invasion of the lower intestinal tract.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Oral or parenteral compositions can be provided in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of pharmaceutical compounds containing a fusion protein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to non-target cells (e.g., cells that are not undergoing an undesirable inflammatory reaction) and, thereby, reduce side effects. In general, the fusion proteins described herein should be well-tolerated by an animal (e.g., mouse, non-human primate, or human).

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models (e.g., of infection or inflammatory disease) to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or ELISA.

As defined herein, a therapeutically effective amount of a fusion protein (i.e., an effective dosage) is an amount sufficient to exert a therapeutically beneficial effect. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a fusion protein can include a single treatment or can include a series of treatments.

Generally, partially and fully human fusion proteins are expected to have a longer half-life within the human body are used for treatment of humans. Accordingly, lower dosages and less frequent administration is often possible. Modifications such as lipidation can be used to stabilize a fusion protein and to enhance uptake and tissue penetration (e.g., into the brain). A method for lipidation of antibodies is described by Cruikshank et al. (1997, J. Acquired Immune Deficiency Syndromes and Human Retrovirology 14:193) and can be adapted for use with fusion proteins. Another method for increasing stability is to conjugate the fusion protein with human serum albumin The pharmaceutical compositions can be included in a container, pack, or dispenser together with instructions for administration.

Treatment Methods and Compositions

Provided herein are methods and compositions for both prophylactic and therapeutic methods of treating a subject at risk of (or susceptible to) a disorder or having a disorder associated with a pathogen, e.g., as described herein, including gonorrhea, meningococcal meningitis or sepsis, influenza, pertussis (whooping cough), pneumonia, *pseudomonas* infection, or a yeast infection, as a result of infection, e.g. with *N. gonorrhoeae, N. meningitidis, P. aeruginosa, H. influenzae, B. pertussis, S. pneumonia* or *C. albicans.*

As used herein, the term "treatment" is defined as the application or administration of a therapeutic agent (e.g., an agent comprising a fusion protein) to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent can be a fusion protein, a recombinant nucleic acid encoding a fusion protein, or a fusion protein that has been modified as described herein.

Pathogens that can be targeted using the fusion proteins described herein include microbes, e.g., gram-positive and gram-negative bacteria, including, but not limited to, *Pseudomonas aeruginosa, Streptococcus pneumoniae, Escherichia coli, Salmonella typhimurium, Neisseria meningitidis, Neisseria gonorrhoeae, Haemophilus influenzae* and *Staphylococcus aureus*; fungi such as *Aspergillus fumigatus, Candida albicans,* spirochetes including *Borrelia burgdorferi,* and parasites including *Plasmodium falciparum.* Any pathogen that binds the complement inhibitor factor H (FH) to evade complement-dependent killing can be targeted with a fusion protein as described herein.

A fusion protein can be delivered to a subject at risk for developing a disorder (e.g., after exposure to a biological weapon (e.g., *Francisella tularensis* (causes tularemia)) or a microbe that can cause illness, or before major surgery) or to treat an existing condition. Fusion proteins can be delivered using methods known in the art, for example, systemically, or by direct delivery to a desired site such as joint or other area of a subject's body in which it is desirable to inhibit a pathogen-related response such as inflammation, e.g., by injection or inhalation, e.g., of an aerosol; delivery by an aerosol may be particularly useful in the case of exposure to an airborne pathogen.

Fusion proteins can also be delivered using a recombinant particle such as a recombinant adenovirus containing an expressible nucleic acid sequence encoding the fusion protein. Such methods are known in the art (e.g., U.S. Pat. No. 5,998,598).

The fusion proteins described herein can also be used for the preparation of a medicament for use in any of the methods of treatment described herein.

Liquid Purification Therapy

The methods of treating disorders associated with a pathogen as described herein include the use of liquid, e.g., blood, purification methods. These methods can include temporarily removing blood from a subject, treating the blood with a fusion protein to remove soluble FH ligands and pathogens, and returning the blood to the subject. General methods for performing such purifications (sometimes referred to as "apheresis") are known in the art, and typically involve passing the blood over a column or other device to extract a selected impurity, see, e.g., U.S. Pat. No. 6,569,112 (Strahilevitz); Asahi et al., Therapeutic Apheresis 7(1):74-77(5), 2003; Hout et al., ASAIO J., 46(6):702-206, 2000; Matsuo et al., Therapeutic Apheresis and Dialysis 8(3):194, 2004. These methods can be adapted for use in the present method. For example, a column or solid substrate including the fusion protein can be constructed using methods known in the art, and the blood can be passed through it, removing a substantial amount of the FH ligands and/or pathogens present in the blood.

Alternatively, a collectible substrate, e.g., beads, e.g., magnetic beads, can be coated with the fusion protein, and the blood can be mixed with the beads, and the beads then extracted to removed the FH ligands and pathogens. In some embodiments, the blood is separated into its components before being passed over the column or contacted with the beads. In some embodiments, the methods can be used to remove FH ligands and pathogens from the blood, by using a column or other collectible substrate with covalently linked fusion proteins, which will pull FH ligands and pathogens out of the blood. In some embodiments, more than one type of fusion protein is used, and more than one type of FH ligand or pathogen is removed.

One of skill in the art will appreciate that these methods and other known fluid, e.g., liquid or gas, collection and filtering methods can also be adapted to include the fusion proteins described herein for use in purifying liquids other than blood, e.g., water or any beverage, or media for use in culturing cells, as well as gases, such as air.

Methods of Diagnosis

Fusion proteins as described herein can be used for diagnostic purposes. Thus, included herein are methods for diagnosing a disorder associated with a FH-binding pathogen. The methods include obtaining a sample from a subject, contacting the sample with a fusion protein as described herein under conditions sufficient to allow the fusion protein and pathogen to form complexes, and evaluating the presence and/or level of a pathogen that binds to FH in the sample by detecting the complexes. The methods can also include comparing the presence and/or level with one or more references, e.g., a control reference that represents a normal level of FH-binding pathogen, e.g., a level in an unaffected subject (typically non-detectable), and/or a disease reference that represents a level of FH ligand or pathogen, associated with the disorder, e.g., a level in a subject having a disorder associated with the pathogen. The presence and/or level of a protein can be evaluated using methods described herein, or other methods known in the art.

In some embodiments, the presence and/or level of FH-binding pathogen is comparable to the presence and/or level of FH-binding pathogen in the disease reference, and if the subject also has one or more symptoms associated with a pathogen associated disorder, then the subject has a pathogen associated disorder. In some embodiments, the subject has no overt signs or symptoms of a pathogen associated disorder, but the presence and/or level of FH-binding pathogen is comparable to the presence and/or level of FH-binding pathogen in the disease reference, then the subject has a pathogen associated disorder. In some embodiments, the sample includes a biological fluid, e.g., blood, semen, urine, and/or cerebrospinal fluid. In some embodiments, once it has been determined that a person has a pathogen associated disorder, then a treatment, e.g., as known in the art or as described herein, can be administered.

Also included herein are methods for detecting a FH-binding pathogen in biological or other samples, e.g., fluids such as blood, cell culture media, beverages, water, or air. The methods include obtaining a sample, and evaluating the presence and/or level of the FH-binding pathogen in the sample using an assay described herein, e.g., an assay that detects the presence and/or level of FH-binding pathogen in the sample by detecting the presence of a fusion protein/FH-binding pathogen complex. In some embodiments, the methods include comparing the presence and/or level with one or more references, e.g., a control reference that represents a preselected level, e.g., a level above which the fluid is unsafe to use. These methods can be used in place of, or in addition to, e.g., Limulus amoebocyte lysate assays, which have limited use in blood (see, e.g., Hurley, Clinical Microbiology Reviews, 8(2):268-292 (1995).

In some embodiments, the sample is from a subject, and the presence of FH-binding pathogen in the sample indicates that the subject has a pathogen-associated disorder. These methods have the advantage that FH-binding pathogens from a wide variety of pathogens may be detected, as opposed to methods such as PCR-based methods that may only detect one or a subset of pathogens. In some embodiments, the assay is a simple yes/no assay, and the results indicate that FH-binding pathogen is present in an unacceptable level. In some embodiments, the assay indicates what level of FH-binding pathogen is present.

Kits

Kits based on the fusion protein compounds described herein can be developed and used, e.g., to screen biological fluids from infected (septic) patients, body fluids, or water or food, to name a few applications. The fusion proteins described herein can be used to detect a broad range of microorganisms including mycobacteria and fungi and so can be provided as reagents in a kit for detecting the presence of such microorganisms.

A kit containing a fusion protein can include one or more types of fusion proteins and a standard. The fusion protein can be packaged in a suitable container. The kit can also include instructions for using the kit to detect the presence of a pathogen, e.g., a microorganism or a class or microorganisms.

EXAMPLES

The invention is further described in the following examples, which do not limit the scope of the invention described in the claims.

Materials and Methods

The following materials and methods were used in the Examples set for the below.

Bacterial Strains.

N. gonorrhoeae strains used in this study and their relevant characteristics are listed in Table 1. Strains from the sexually transmitted infection clinic in Nanjing, China were a randomly selected convenience sample. N. gonorrhoeae multiantigen sequence type (NG-MAST) was determined by DNA sequencing of variable regions of porB and tbpB, as previously described (30). An opacity protein (Opa)-negative mutant derivative of strain FA1090 where all 11 opa genes were inactivated was provided by Dr. Janne G. Cannon (University of North Carolina, Chapel Hill, N.C., USA) (31). Bacteria that had been grown on chocolate agar supplemented with IsoVitalex® in an atmosphere enriched with 5% $CO_2$ for ~15 h at 37° C. were suspended in gonococcal liquid media and grown to the mid-log phase, as described previously (32). Sialylation of gonococcal LOS was achieved by adding CMP-Neu5Ac to a final concentration of 2 ug/ml to the growth media. Bacteria were washed and suspended in Hanks' balanced salt solution (HBSS) containing 0.15 mM $CaCl_2$ and 1 mM $MgCl_2$ (HBSS') for use in binding and bactericidal assays.

TABLE 1

N. gonorrhoeae strains used in this study

| Strain | NG-MAST sequence type | Ceftriaxone MIC (ug/ml) | Reference |
|---|---|---|---|
| F62 | 915 | NT[A] | (A) |
| 252 | ND[C] | NT | (B) |
| MS11 | 4813 | 0.032 | (C) |
| FA1090 | 773 | 0.004 | (D) |
| FA1090 Opa⁻ | 773 | NT | (E) |
| CTXr (Spain) | 1407 | 2 (resistant) | (F) |
| H041 | 4220 | 2-4 (resistant) | (G) |
| NJ-1[B] | 3366 | 0.023 | (H) |
| NJ-11 | 270 | 0.047 | (H) |
| NJ-15 | New #1[D] | 0.047 | (H) |
| NJ-19 | New #2[D] | 0.032 | (H) |
| NJ-26 | New #3[D] | 0.032 | (H) |
| NJ-27 | 2318 | 0.064 | (H) |
| NJ-36 | 1766 | 0.032 | (H) |
| NJ-44 | 8736 | 0.125 (elevated MIC to CRO) | (H) |
| NJ-48 | 2008 | 0.125 (elevated MIC to CRO) | (H) |
| NJ-60 | 3289 | 0.380 (resistant) | (H) |

[A]NT, not tested; although an MIC was not obtained, all strains were susceptible to ceftriaxone by the disk-diffusion method
[B]NJ- strains were a random convenience sample from a collection of 64 isolates obtained from men with gonorrhea from an STD clinic in Nanjing, China (8). Ceftriaxone susceptibility was performed by the tested by agar dilution method (8)
[C]ND, not determined.
[D]All new NG-MAST sequence types are distinct from each other having distinct PorB and/or TbpB loci. These sequences have been submitted for NG-MAST allele assignment.

REFERENCES FOR TABLE 1

A. Shafer, W. M., K. Joiner, L. F. Guymon, M. S. Cohen, and P. F. Sparling. 1984. Serum sensitivity of Neisseria gonorrhoeae: the role of lipopolysaccharide. J Infect Dis 149:175-183.

B. McQuillen, D. P., S. Gulati, S. Ram, A. K. Turner, D. B. Jani, T. C. Heeren, and P. A. Rice. 1999. Complement processing and immunoglobulin binding to Neisseria gonorrhoeae determined in vitro simulates in vivo effects. J Infect Dis 179:124-135.

C. Schneider, H., J. M. Griffiss, J. W. Boslego, P. J. Hitchcock, K. M. Zahos, and M. A. Apicella. 1991. Expression of paragloboside-like lipooligosaccharides may be a necessary component of gonococcal pathogenesis in men. J Exp Med 174:1601-1605.

D. Hitchcock, P. J., S. F. Hayes, L. W. Mayer, W. M. Shafer, and S. L. Tessier. 1985. Analyses of gonococcal H.8 antigen: surface location, inter- and intrastrain electrophoretic heterogeneity, and unusual two-dimensional electrophoretic characteristics. J. Exp. Med. 162:2017-2034.

E. Lewis, L. A., S. Ram, A. Prasad, S. Gulati, S. Getzlaff, A. M. Blom, U. Vogel, and P. A. Rice. 2008. Defining targets for complement components C4b and C3b on the pathogenic neisseriae. Infect Immun 76:339-350.

F. Camara, J., J. Serra, J. Ayats, T. Bastida, D. Carnicer-Pont, A. Andreu, and C. Ardanuy. 2012. Molecular characterization of two high-level ceftriaxone-resistant Neisseria gonorrhoeae isolates detected in Catalonia, Spain. J Antimicrob Chemother 67:1858-1860.

G. Ohnishi, M., D. Golparian, K. Shimuta, T. Saika, S. Hoshina, K. Iwasaku, S. Nakayama, J. Kitawaki, and M. Unemo. 2011. Is Neisseria gonorrhoeae initiating a future era of untreatable gonorrhea?: detailed characterization of the first strain with high-level resistance to ceftriaxone. Antimicrob Agents Chemother 55:3538-3545.

H. Li, S., X. Su, W. Le, F. Jiang, B. Wang, and P. A. Rice. 2014. Antimicrobial susceptibility of Neisseria gonorrhoeae isolates from symptomatic men attending the Nanjing sexually transmitted diseases clinic (2011 inverted question mark2012): genetic characteristics of isolates with reduced sensitivity to ceftriaxone. BMC Infect Dis 14:622.

Normal Human Serum (NHS).

Serum was obtained from normal healthy adult volunteers with no history of gonococcal or meningococcal infection who provided informed consent. Participation was approved by the University of Massachusetts Institutional Review Board for the protection of human subjects. Serum was obtained by allowing blood to clot at 25° C. for 30 min followed by centrifugation at 1500 g for 20 min at 4° C. Sera were pooled and stored at −70° C.

IgG and IgM Depleted Human Serum (Human Complement).

To study the effects of the FH18-20/Fc proteins without confounding by natural anti-gonococcal antibodies present in NHS, we depleted IgG and IgM from freshly collected human serum, as described previously (33). Briefly, EDTA (final concentration 10 mM) and NaCl (final concentration 1 M) were added to freshly prepared human serum and treated sera was passed first over anti-human IgM agarose (Sigma), followed by passage through protein G-Sepharose; both columns were equilibrated in PBS containing 10 mM EDTA and 1 M NaCl. NaCl was added to minimize C1q depletion during passage of serum through the anti-human IgM column. The flow-through was collected, spin concentrated and dialyzed against PBS/0.1 mM EDTA to its original volume using a 10-kDa cutoff Amicon Ultra-15 centrifugal filter device (Millipore, Bedford, Mass.), sterilized by passage through a 0.22-µm filter (Millipore), aliquoted and stored at −70° C. Hemolytic activity was confirmed using a total complement hemolytic plate assay (The Binding Site Inc., Birmingham, U.K). Depletion of IgG and IgM was confirmed by dot-blot assays. In some experiments, complement activity of serum was destroyed by heating serum at 56° C. for 1 h.

Expression and Purification of FH/Fc Fusion Proteins.

Cloning, expression and purification of a chimeric protein comprising human FH (HuFH) domains 18-20 fused to mouse IgG2a Fc has been described previously (23). Briefly, the DNA encoding FH domains 18-20 was cloned into AscI-NotI sites of eukaryotic expression vector pCDNA3 containing the sequence encoding mouse IgG2a Fc (34). We created four HuFH18-20/Fc mutants using the Quickchange site-directed mutagenesis kit (Agilent Technologies) according to the manufacturer's instructions with primers D1119G, R1182S, W1183R and R1215G (Table 2). Mouse IgG2a Fc was replaced by human IgG1 Fc as follows. FH domains 18-20 were amplified using primers FH18EcoRI and FH20hIgGloverlapR, and human IgG1Fc (Invivogen) was amplified with primers FH20hIgGloverlapF and HIgG1NheI (Table 2). The PCR products were then fused together by overlap extension PCR using primers FH18EcoRI and HIgG1NheI. The final PCR product encoding FH18-20 fused to hIgG1 was digested with EcoRI and NheI and cloned into pFUSE-hIgG1-Fc2 (Invivogen). The resulting plasmids were verified by DNA sequencing and used to transiently transfect CHO cells using lipofectin (Life Technologies), according to the manufacturer's instructions. Media from transfected cells was collected after 2 days and FH/Fc was purified by passage over protein A agarose. Mass was determined by Coomassie Blue staining of proteins separated by SDS-PAGE and protein concentrations were determined using the BCA protein Assay kit (Pierce).

previously (35). Data were acquired on a LSRII flow cytometer and data were analyzed using FlowJo software.

Serum Bactericidal Assay.

Serum bactericidal assays were performed as described previously (36). Bacteria that had been harvested from an overnight culture on chocolate agar plates were grown in gonococcal liquid media supplemented with CMP-Neu5Ac (2 ug/ml) from an $OD_{600\ nm}$ of ~0.1 to the mid-log phase ($OD_{600\ nm}$ ~0.25). Approximately 2000 colony forming units (CFUs) of *N. gonorrhoeae* were incubated with human complement in the presence or the absence of the FH/Fc fusion protein (concentration indicated with each experiment). The final volume of the bactericidal reaction mixture was 150 ul. Aliquots of 25-ul reaction mixtures were plated onto chocolate agar in duplicate at the beginning of the assay (to) and again after incubation at 37° C. for 30 min ($t_{30}$). Survival was calculated as the number of viable colonies at $t_{30}$ relative to to.

Hemolytic Assay.

Lysis of human erythrocytes was measured using a method similar to one described previously (37). Freshly isolated human red blood cells (RBCs) ($5 \times 10^6$) were incubated with 7 ug/ml anti-CD59 monoclonal antibody (mAb) (clone MEM43; Abcam) at 4° C. for 20 min and then mixed, on ice, with NHS derived from the homologous donor (final NHS concentration 40%), gelatin veronal buffer (GVB), 5 mM $MgCl_2$ and 5 mM EGTA and the indicated concentrations of FH/Fc. The mixture was then transferred to a 37° C. water bath and incubated for 20 min. GVB-EDTA (200 ul) was added to a final concentration of 10 mM EDTA to block further complement activation and the samples were immediately centrifuged at 4° C. and the $OD_{410\ nm}$ of the super-

TABLE 2

Primers used for construction of FH/Fc fusion proteins

| Primers | Sequence | SEQ ID NO: |
|---|---|---|
| D1119G | 5'-CACCTATTGACAATGGGGGCATTACTTCATTCCCGTT-3' | SEQ ID NO: 7 |
| R1182S | 5'-ATTATGGAAAATTATAACATAGCATTAAGCTGGACAGCCAAACAGAAG-3' | SEQ ID NO: 8 |
| W1183R | 5'-AAAATTATAACATAGCATTAAGGAGGACAGCCAAACAGAAGCTTTAT-3' | SEQ ID NO: 9 |
| R1215G | 5'-CACGTTCTCACACATTGGGAACAACATGTTGGGAT-3' | SEQ ID NO: 10 |
| FH18EcoRI | 5'-GAATTCGTGTGTGAATCCGCCCACAGTAC-3' | SEQ ID NO: 11 |
| FH20hIgG1 overlapF | 5'-AGCCCAAATCTTG TGACAAAACTCACACATGCCCA-3' | SEQ ID NO: 12 |
| FH20hIgG1 overlapR | 5'-GCCGCGGGGGGCGAGCCCAAATCTTGTGACAA-3' | SEQ ID NO: 13 |
| HIgG1NheI | 5'-CGGGTAAATGAGTGCTAGCTGG-3' | SEQ ID NO: 14 |

Antibodies.

Sheep anti-human C3c-FITC was from AbD Serotec (cat. #AHP031F), anti-mouse IgG FITC and anti-human IgG FITC were from Sigma. Both antibodies (Abs) were used at a dilution of 1:200 in HBSS' and 1% bovine serum albumin (BSA) (HBSS++/BSA) in flow cytometry assays.

Flow Cytometry.

Binding of FH/Fc to bacteria and C3 fragments deposited on bacteria were measured by flow cytometry as described natants was determined. Background lysis (anti-CD59-treated RBCs plus buffer alone) was subtracted from each reading and the results were expressed as $OD_{410\ nm}$.

Opsonophagocytosis Assay.

Heparinized venous blood was obtained from a healthy adult volunteer in accordance with a protocol approved by the Institutional Review Board for the protection of human subjects at the University of Massachusetts. Polymorphonuclear leukocytes (PMNs) were isolated using Mono-Poly® resolving medium (MP Biomedicals, LLC) according to the manufacturer's instructions. Isolated PMNs were washed and suspended in HBSS without added divalent cations, counted, and diluted to $1\times10^7$/ml in HEPES-buffered RPMI-1640 medium supplemented with L-glutamine and 1% heat-inactivated fetal bovine serum (FBS). To measure survival of gonococci in the presence of PMNs, an Opacity protein (Opa)-negative mutant of N. gonorrhoeae strain FA1090 that was grown in media containing 2 ug/ml CMP-Neu5Ac to sialylated LOS was added to $1\times10^6$ PMNs at an multiplicity of infection (MOI) of 10 (10 bacteria to 1 PMN). Opa-negative N. gonorrhoeae was used because select Opa proteins serve as ligands for human carcinoembryonic antigen-related cell adhesion molecule 3 (CEACAM3) that is expressed by PMNs, which results in phagocytosis (38). FHD1119G/HuFc was added at a concentration of 16.7 µg/ml, followed by 10% human complement (prepared as described above). Bacteria plus PMNs and 10% NHS (Ab intact) was used as a positive control for killing. The reaction mixtures were incubated for 60 min at 37° C. in a shaking water bath. Bacteria were serially diluted and plated at 0 and 60 min on chocolate agar plates. Percent survival of gonococci in each reaction was calculated as a ratio of CFUs at 60 min to CFUs at the start of the assay (0 min).

Mouse Vaginal Colonization Model.

Use of animals in this study was performed in strict accordance with the recommendations in the Guide for the Care and Use of Laboratory Animals of the National Institutes of Health. The protocol was approved by the Institutional Animal Care and Use Committee (IACUC) at the University of Massachusetts Medical School. Female BALB/c mice 5-6 weeks of age (Jackson Laboratories) in the diestrus phase of the estrous cycle were started on treatment (that day) with 0.5 mg Premarin (Pfizer) in 200 µl of water given subcutaneously on each of three days; –2, 0 and +2 days (before, the day of and after inoculation) to prolong the estrus phase of the cycle and promote susceptibility to Ng infection. Antibiotics (vancomycin, colistin, neomycin, trimethoprim and streptomycin) ineffective against Ng were also used to reduce competitive microflora (39). Mice (n=26) were then infected with $1.5\times10^6$ CFU of strain F62. One group of mice (n=14) was treated with 12 FHD1119G/mouse IgG2a Fc (1.5 mg/ml in PBS) daily intravaginally while the remaining 12 mice were given a corresponding volume of PBS (vehicle controls). We used a construct containing mouse IgG2a Fc (and opposed to human IgG1 Fc used in the bactericidal and opsonophagocytosis assays) to maintain species congruity between Fc and its cognate FcR. Initial experiments with systemic administration of FH/Fc to wild-type mice resulted in the generation of anti-FH Ab, which led us to administer the therapeutic locally. Finally, we administered 10 µg of CMP-Neu5Ac locally to each mouse daily along with the FH/Fc or PBS control to ensure LOS substitution with Neu5Ac. This is because mice, but not humans, possess an enzyme called CMP-N-acetylneuraminic acid hydroxylase (CMAH) that converts CMP-Neu5Ac to CMP-N-glycolylneuraminic acid (CMP-Neu5Gc) (40-42). CMAH activity, and therefore the relative amounts of these two CMP-sialic acids, varies across tissues (43). Thus, while mice express both CMP-Neu5Ac and CMP-Neu5Gc, humans make only CMP-Neu5Ac. Both these CMP-sialic acids can serve as substrates for gonococcal LOS sialyltransferase, therefore gonococcal LNT LOS can be substituted with either Neu5Ac or Neu5Gc ($$ REF). In contrast, a mutation in humans results in inactivation of CMAH (41) and as a result gonococcal LOS in humans is exclusively substituted with Neu5Ac. Administering CMP-Neu5Ac would result in more 'human-like' LNT LOS substitution with Neu5Ac.

Statistics.

Experiments that compared clearance of N. gonorrhoeae in independent groups of mice estimated and tested three characteristics of the data (44): Time to clearance, longitudinal trends in mean $\log_{10}$ CFU and the cumulative CFU as area under the curve (AUC). Statistical analyses were performed using mice that initially yielded bacterial colonies on Days 1 and/or 2. Median time to clearance was estimated using Kaplan-Meier survival curves; the times to clearance were compared between groups using a log-rank test. Mean $\log_{10}$ CFU trends over time were compared between groups using a linear mixed model with mouse as the random effect using both a random intercept and a random slope. A cubic function in time was determined to provide the best fit; random slopes were linear in time. A likelihood ratio test was used to compare nested models (with and without the interaction term of group and time) to test whether the trend differed over time between the two groups. The mean AUC ($\log_{10}$ CFU versus time) was computed for each mouse to estimate the bacterial burden over time (cumulative infection); the means under the curves were compared between groups using the nonparametric rank sum test because distributions were skewed or kurtotic.

Example 1. Selection of the FHD1119G/Fc as the Lead FH/Fc Therapeutic Molecule

We showed previously that a chimeric molecule comprising FH domains 18, 19 and 20 fused to murine Fc bound to and mediated complement-dependent killing of N. gonorrhoeae strains F62 and 252 (27). However, the C-terminal domains of FH (domains 19 and 20) can bind to C3b/C3d (19, 45), heparin/heparan sulfate-containing surfaces (46), and endothelial cells (47) and protects host cells from complement attack. Thus, if left unmodified in the context of FH/Fc, the C-terminal domains of FH (domains 19 and 20) will compete with binding and function of the full-length FH on human cells. Competition for the binding and function of full-length FH by a recombinant FH molecules comprising domains 19 and 20 was shown on RBCs treated with anti-CD59 (erythrocytes treated with anti-CD59 rely on binding of FH to regulate complement activation and hemolysis) (37). Therefore, we sought to define mutations in FH18-20 that eliminated complement activation on host cells while maintaining the ability to bind to and mediate killing of N. gonorrhoeae.

Figure 1B:
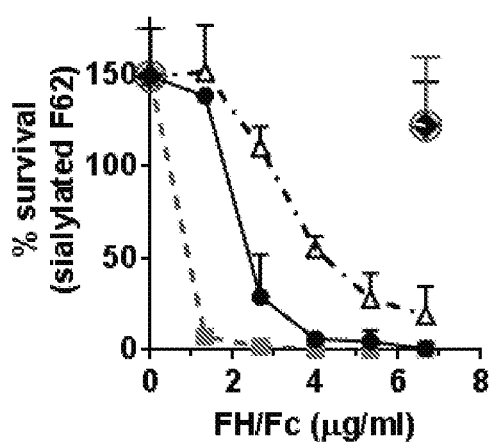
Figure 1C:
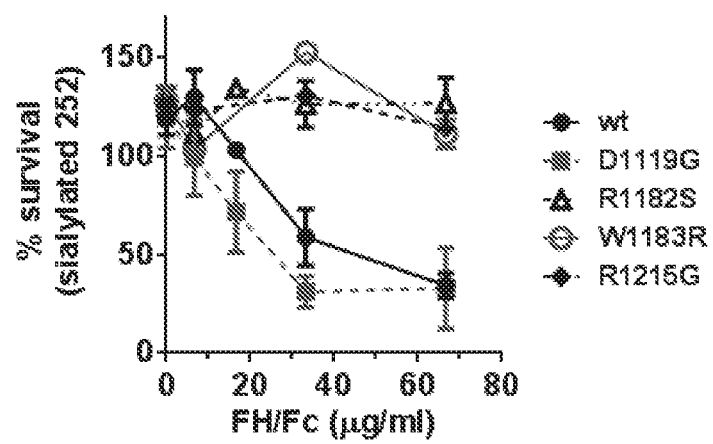

Atypical hemolytic uremic syndrome (aHUS) is a condition that results from 'over-activity' of the alternative pathway of complement. Mutations of FH that affects FH binding to glycosaminoglycans and/or C3 fragments on host cells are important causes for the development of aHUS (reviewed in references (48-50)). Our choice of mutations was guided by some of the aHUS mutations in FH domains 19 and 20 that were characterized by Ferreira et al (37). They introduced these mutations into recombinant molecules that comprised FH domains 19 and 20, and examined whether the mutant molecules could block full-length human FH from protecting anti-CD59-treated human RBCs from complement-mediated hemolysis (37). As expected, the wild-type FH 19-20 out-competed the full-length FH and resulted in hemolysis. Four mutant molecules, D1119G (domain 19), R1182S, W1183R and R1215G (the latter three in domain 20) did not interfere with the normal function of native FH (37), which led us to focus on these four aHUS mutations. FH18-20/murine IgG2a Fc proteins that contained these individual mutations were expressed in CHO cells and purified from tissue culture supernatants; the molecular masses and purity of the proteins was determined by SDS-PAGE stained with Coomassie Blue (data not shown). Bacteria were grown in media containing CMP-Neu5Ac, which results in sialylation of LNT LOS, similar to sialylation that occurs in vivo (20). We compared binding of FH18-20/Fc mutant proteins to sialylated gonococci with binding of the wild-type (WT) FH18-20/Fc (FIG. 1A). Two mutant proteins, FHD1119G/Fc and FHR1182S/Fc showed similar binding to sialylated *N. gonorrhoeae* strain F62 compared to the wild-type protein (FH18-20/Fc). The FH/Fc molecules bearing the W1183R or R1215G mutations, showed weak and no binding to sialylated strain F62 respectively, (FIG. 1A). FH/Fc mutated proteins were tested for complement-dependent killing of sialylated strain F62 (FIG. 1B, left graph). Consistent with our previous work (27), the wild-type molecule (FH18-20/Fc) killed strain F62 in a dose-responsive manner (FIG. 1B); FHD1119G/Fc and FHR1182S/Fc also both killed sialylated strain F62. Neither FHR1183R/Fc or FHR1215/Fc, killed sialylated strain F62 when used at maximal concentration (6.7 ug/ml).

The killing curves, in particular for the wild-type molecule and the D1119G mutant for sialylated strain F62, were steep—i.e., small differences in FH/Fc concentration resulted in dramatic increases in complement-dependent killing. To ascertain superiority of function of FHD1119G/Fc mutant over FHR1182S/Fc mutant, we used strain 252 that is intrinsically more resistant to killing by complement than F62 (36, 51). As shown in (FIG. 1B, right graph), only the wild-type molecule and the D1119G mutant possessed activity against sialylated strain 252. Thus, FHD1119G/Fc represented our lead molecule and was studied further.

Example 2. FHD1119G/Fc does not Cause Hemolysis

Figure 8:
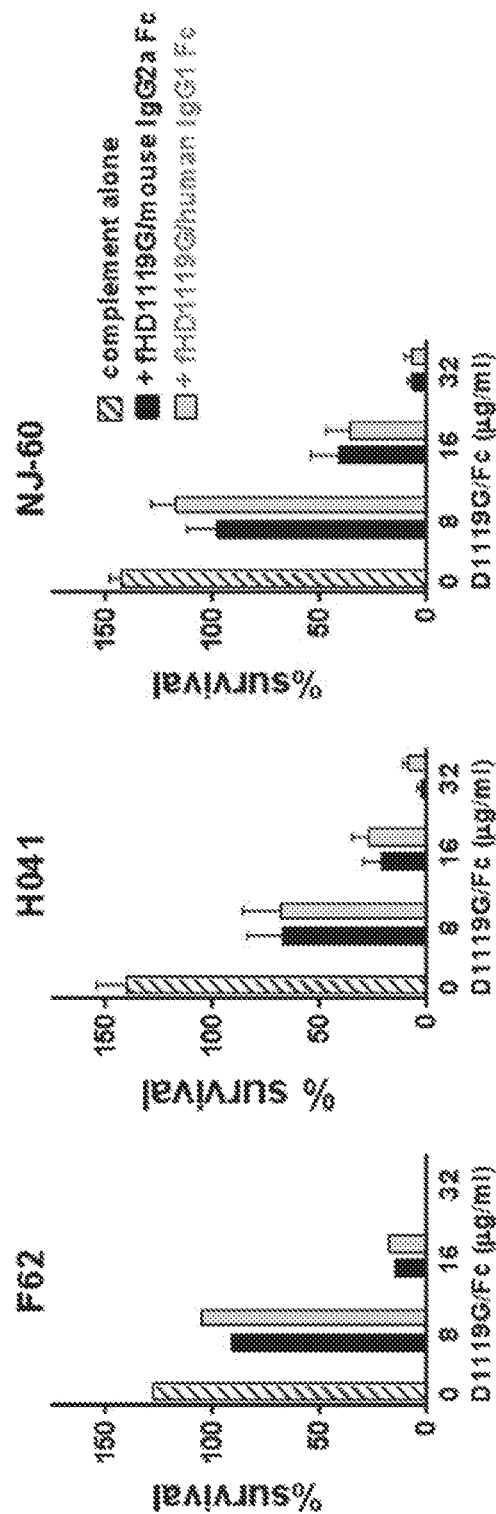
FIG. 8. FHD1119G/human IgG1 Fc and FHD1119G/mouse IgG2a Fc have comparable bactericidal activities. Survival of sialylated N. gonorrhoeae F62, H041 and NJ-60 in increasing concentrations of FHD1119G fused to either human IgG1 Fc (grey bars) or mouse IgG2a Fc (black bars) was determined following the addition of 17% (v/v) pooled normal human serum (NETS; not depleted of natural Ab). Percent survival of bacteria at 30 min relative to to is shown on the Y-axis (mean [SD] of 2 separately performed experiments). Reaction mixtures containing bacteria and pooled NETS are indicated by hatched bars.

Having identified the D1119G mutant (FHD1119G/Fc) as the molecule with the best bactericidal activity among the mutants tested, we next asked whether this mutation eliminated toxicity to host cells, as measured by the human RBC lysis assay described by Ferreira et al (37). Complement-mediated lysis of human RBCs was measured in the presence of NHS and FHD1119G/Fc or the control wild type FH18-20/Fc (FIG. 2). Two FHD1119G/Fc chimeric molecules were tested—one that contained mouse IgG2a Fc and a second containing human IgG1 Fc. The latter was developed for use in studies with human PMNs (see below) and in anticipation of possible use as a therapeutic antimicrobial in humans. FIG. 2 shows lysis of RBCs when mouse FH18-20/Fc (WT) protein was added to the reaction mixture (positive control); FHD1119G/Fc proteins (mouse or human Fc) did not cause measurable lysis over baseline levels (controls with buffer alone) at any concentration tested (0-66.7 ug/ml). FHD1119G/mouse IgG2a Fc and FHD1119G/human IgG1 Fc exhibited similar bactericidal activities against three different strains of *N. gonorrhoeae* (FIG. 8). FHD1119G/human IgG1 Fc was used in subsequent experiments.

Example 3. Binding of FHD1119G/Fc to *N. gonorrhoeae*

Figure 3:
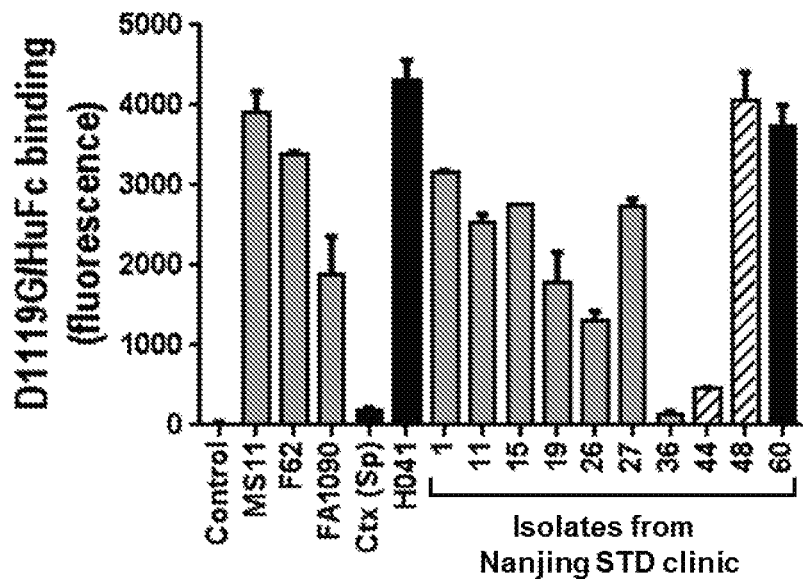
FIG. 3. Binding of FHD1119G/human Fc to strains of sialylated *N. gonorrhoeae*. Binding of FHD1119G/human IgG1 Fc (10 ug/ml) was measured by flow cytometry. Y-axis represents median fluorescence (mean [SD] of 2 independently performed experiments). 'Control' represents a reaction mixture lacking FH/Fc. Strains that are resistant to ceftriaxone (MIC>0.25 µg/ml) are indicated by solid black bars, strains that show elevated MICs to ceftriaxone (MICs 0.125 ug/ml and 0.25 ug/ml) by hatched bars and ceftriaxone-sensitive isolates (MICs<0.125 ug/ml) by grey shaded bars.
Figure 9:
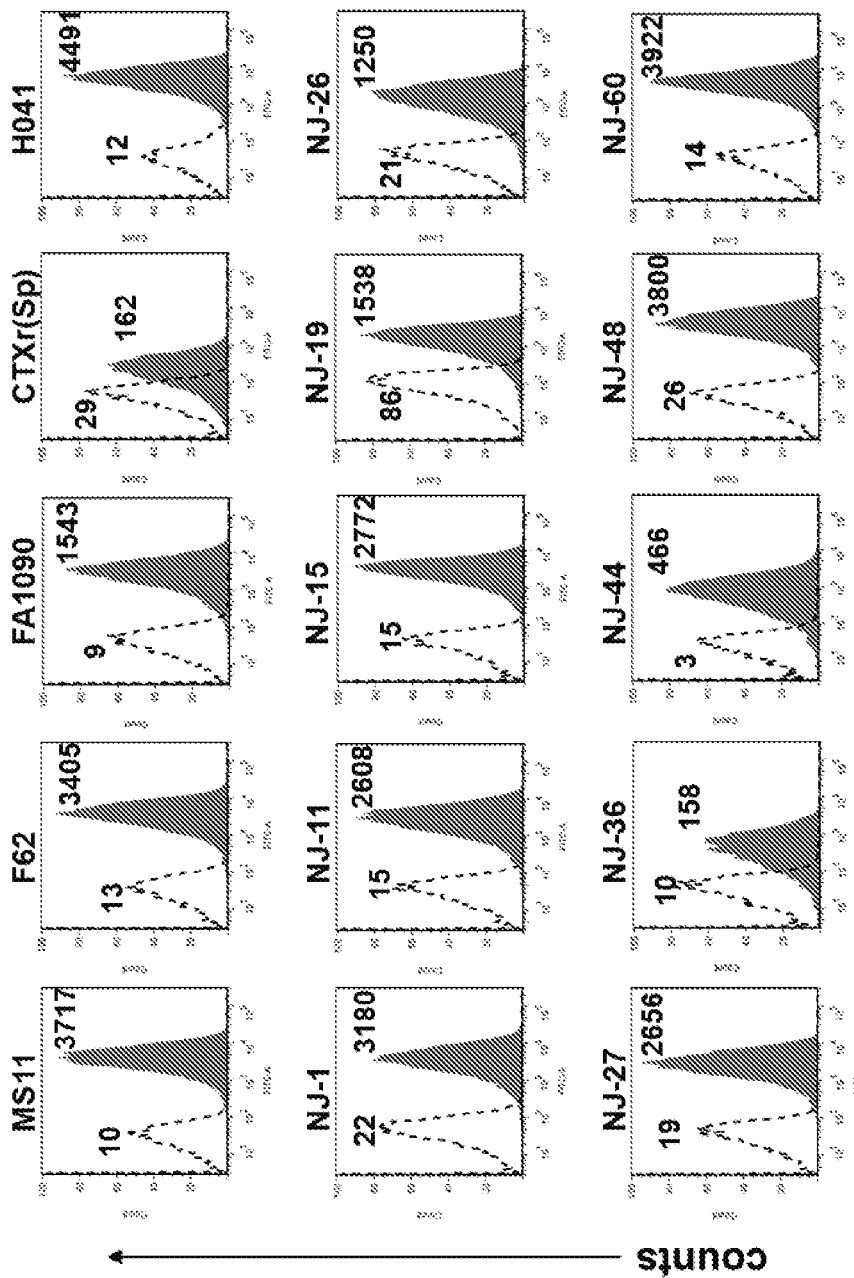
FIG. 9. Representative histogram tracings of binding of FHD1119G/human IgG1 Fc to 15 clinical isolates of N. gonorrhoeae sialylated in vitro. Each of the 15 isolates shown above was incubated with FHD1119G/human IgG1 Fc (10 µg/ml) and bound FH/Fc was detected by flow cytometry using anti-human IgG FITC (grey shaded histograms). Controls, shown by the histograms with the broken lines, represent reaction mixtures lacking FH/Fc. The numbers alongside the histograms represents the median fluorescence of the entire bacterial population.

A clinically useful anti-bacterial immunotherapeutic should possess activity against a wide repertoire of clinically relevant strains. We next tested binding of FHD1119G/human IgG1 Fc to 15 clinical isolates of *N. gonorrhoeae* (listed in Table 1), including three contemporary ceftriaxone-resistant isolates: CTXr(Sp) (4), H041 (7), and NJ-60 (52) and two isolates with elevated MICs to ceftriaxone (NJ-44 and NJ-48) (52). All strains were grown in media supplemented with 2 ug/ml CMP-Neu5Ac to sialylate LOS, as occurs in vivo (20, 21). Although the binding of FHD1119G/HuFc varied across strains, binding was seen to all sialylated strains that were tested in a flow cytometry assay (≈6 to 346-fold fluorescence increase over control values; FIG. 3). Representative histogram tracings from a flow cytometry experiment are shown in FIG. 9.

Example 4. Bactericidal Activity of D1119G/Fc Against *N. gonorrhoeae*

Figure 4:
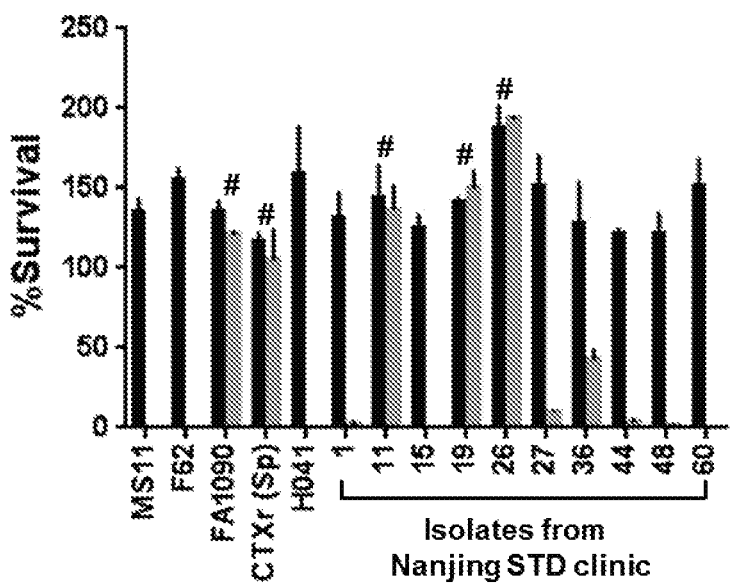
FIG. 4. Complement-dependent bactericidal activity of FHD1119G/Fc against *N. gonorrhoeae*. Sialylated *N. gonorrhoeae* strains (same strains as in FIG. 4) were incubated with FHD1119G/human IgG1 Fc (33.3 µg/ml; grey bars) or buffer alone (controls; black bars), followed by the addition of 20% (v/v) human complement for 30 min at 37° C. Percent survival of bacterial counts at 30 min relative to counts at the beginning of the assay (to min) is shown on the Y-axis (mean±SEM of at least 2 separately performed experiments). Strains that resisted killing by FHD1119G/Fc plus complement (>50% survival of CFU at 30 min) are indicated ("#").

FHD1119G/Fc was tested for complement dependent killing of the 15 sialylated clinical isolates of *N. gonorrhoeae* (FIG. 4). Ten of 15 strains showed from 0% to <50% survival (50%-100% killing) compared to baseline survival (bacteria plus human complement (normal human serum depleted of IgG and IgM) alone) (FIG. 4), while the remaining 5 strains (FA1090, CTXr (Sp), NJ-11, NJ-19 and NJ-26) survived >50% in the presence of FHD1119G/Fc (marked with an "#" in FIG. 4). It is worth noting that the amount of binding of FHD1119G/Fc did not correlate with bacterial killing.

Example 5. C3 Fragment Deposition Mediated by FHD1119G/Fc on *N. gonorrhoeae* Resistant to Direct Complement-Dependent Lysis Complement-dependent opsonophagocytosis may also contribute to clearance of gonococci in humans. We sought to determine whether the 5 isolates that resisted direct killing by complement (mediated by insertion of the membrane attack complex [C5b-9]), had also resisted deposition of C3. Sialylated bacteria were incubated either with human complement alone, or complement plus FHD1119G/Fc; C3 fragments deposited on bacteria were measured by flow cytometry (FIG. 5). Minimal C3 was deposited on these strains in the presence of complement alone (compared to baseline antibody conjugate control levels). Addition of FHD1119G/Fc markedly increased C3 fragment deposition. Increases ranged from 13- to 88-fold above levels seen with complement alone. These data suggest that resistance of these strains to direct complement-dependent killing may be the result of a block in complement function distal to C3 deposition.

Example 6. FHD1119G/Fc Enhances Complement-Dependent Killing by PMNs

Having shown that FHD1119G/Fc augments C3 deposition on gonococci, we asked whether it could also facilitate opsonophagocytic killing by human PMNs. Select gonococcal opacity proteins (Opa) can engage human CEACAMs (38, 53). CEACAM3 that is expressed by human PMNs can facilitate uptake and killing of gonococci through Opa in a complement and FcR independent manner (38). To eliminate Opa-CEACAM3 interactions, we used an Opa-negative derivative of strain FA1090 where all 11 opa genes had been inactivated (31). Similar to wild-type FA1090, the isogenic Opa-negative (Opa) mutant of FA1090 also resisted direct complement-dependent killing (>100% survival; data not shown). FHD1119G/Fc increased killing of FA1090 Opa-negative in the presence of active complement and PMNs (FIG. 6). Complement alone or FHD1119G/Fc alone did not facilitate PMN-dependent killing of bacteria, indicating that both complement and Fc were required for opsonophagocytic killing of Opa-negative gonococci by human PMNs in vitro.

Figure 7A:
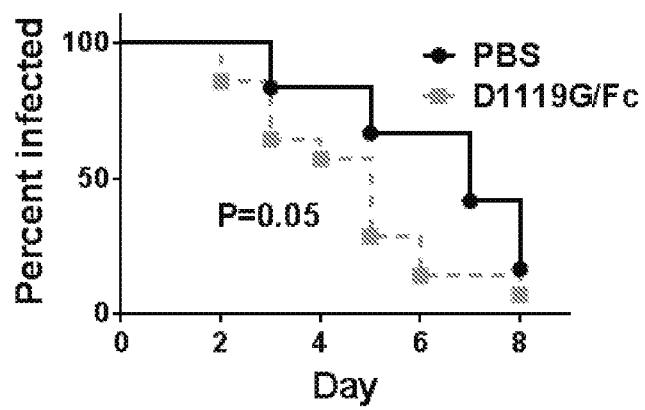
FIGS. 7A-C. FHD1119G/mouse IgG2a Fc reduces the duration and burden of gonococcal infection in the murine vaginal model of gonococcal colonization. Two groups of Premarin-treated wild-type BALB/c mice were infected with $1.5 \times 10^6$ CFU of *N. gonorrhoeae* strain F62 and given either 12 µg FHD1119G/mouse IgG2a Fc (n=14) or a corresponding volume of PBS (n=12) as a vehicle control. Each mouse also received 10 µg of CMP-Neu5Ac daily as described in the Materials and Methods. Vaginal swabs were obtained daily to quantify Ng CFUs. A. Kaplan Meier analysis of time to clearance. B. Colonization of bacteria ($\log_{10}$ CFU) measured daily. C. Bacterial burdens consolidated over time (Area Under the Curve [$\log_{10}$ CFU] analysis) for the two groups.
Figure 7B:
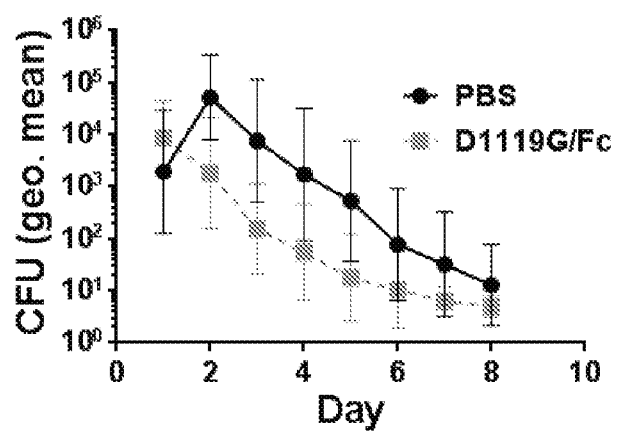
Figure 7C:
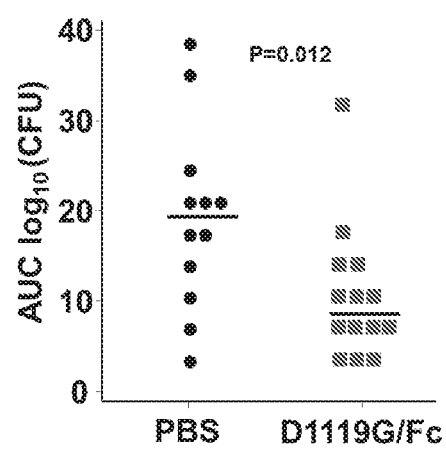

Example 7. FHD1119G/Mouse IgG2a Fc Decreases the Burden and Duration of Gonococcal Infection in the Mouse Vaginal Colonization Model The efficacy of FHD1119G/mouse IgG2a Fc was tested in the mouse vaginal colonization model. The rationale for the use of mouse Fc, intravaginal administration and the concomitant use of CMP-Neu5Ac have all been discussed above in the Materials and Methods. Mice were infected with strain F62 and given either 12 µg of D1119G/Fc daily intravaginally for 7 days (n=14 mice) or PBS as a vehicle control (n=12). As shown in FIG. 7, the group that received FHD1119G/mouse IgG2a Fc cleared the infection faster (FIG. 7A; median time to clearance was 5 days, versus 7 days in the control group; P=0.05; clearance times were compared between groups using a log-rank test). Mixed model analysis indicated significant differences in colonization trends between the two groups comparing D1119G/Fc and PBS-treated groups (P<0.0001; FIG. 7B). A significant difference in the Mean Areas Under the Curve (mean AUCs) (log 10 CFU versus time) between the treated and control groups was also observed (P=0.012; FIG. 7C).

Example 8. FHD1119G/Human IgG1 Fc Decreases the Burden and Duration of Gonococcal Infection of Strains FA1090 and H041 in the Mouse Vaginal Colonization Model To determine whether FHD1119G/human IgG1 Fc and FHD1119G/mouse IgG2a Fc had comparable bactericidal activities, the survival of sialylated $N.$ $gonorrhoeae$ F62, H041 and NJ-60 in increasing concentrations of FHD1119G fused to either human IgG1 Fc or mouse IgG2a Fc was determined following the addition of 17% (v/v) pooled normal human serum (NHS; not depleted of natural Ab). FHD1119G/human IgG1 Fc and FHD1119G/mouse IgG2a Fc have comparable bactericidal activities at all concentrations tested (FIG. 8). Next, the binding of FHD1119G/human IgG1 Fc to 15 clinical isolates of $N.$ $gonorrhoeae$ sialylated was evaluated in vitro. Each of the 15 isolates bound FH/Fc (FIG. 9).

Figure 10A:
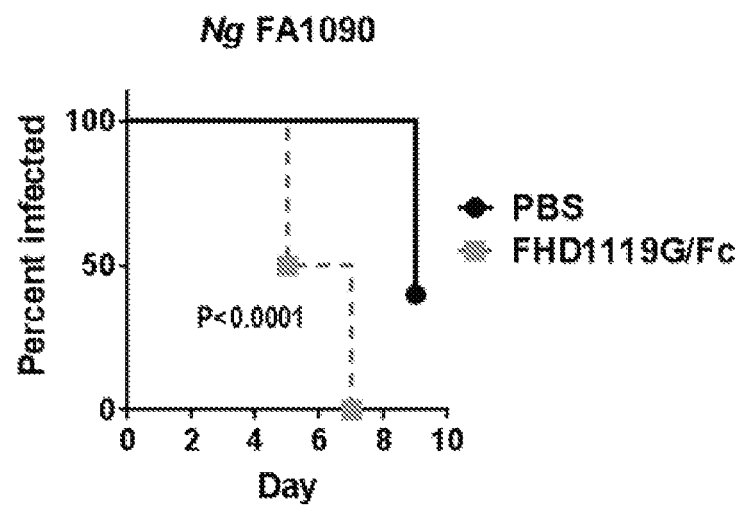
FIGS. 10A-C. Efficacy of FHD1119G/Fc against Ng FA1090. BALB/c mice (n=10/group) were infected with ~$10^6$ CFU of Ng and treated daily intravaginally with PBS (vehicle control) or FHD1119G/human IgG1 Fc (10 µg/day). Vaginal swabs were obtained daily to enumerate viable CFUs. A. Kaplan Meier curve shows time to clearance (Mantel-Cox analysis). B. $\log_{10}$ CFU versus time is shown. C. Bacterial burdens consolidated over time (Area Under Curve ($\log_{10}$ CFU) analysis are shown (comparisons made by Mann-Whitney U test).
Figure 10B:
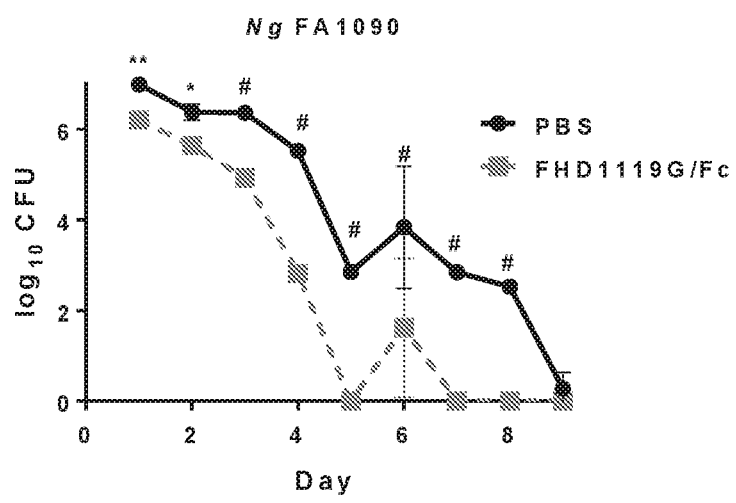
Figure 10C:
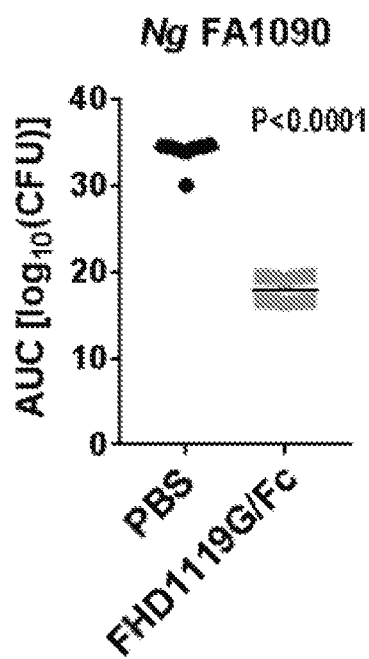
Figure 11A:
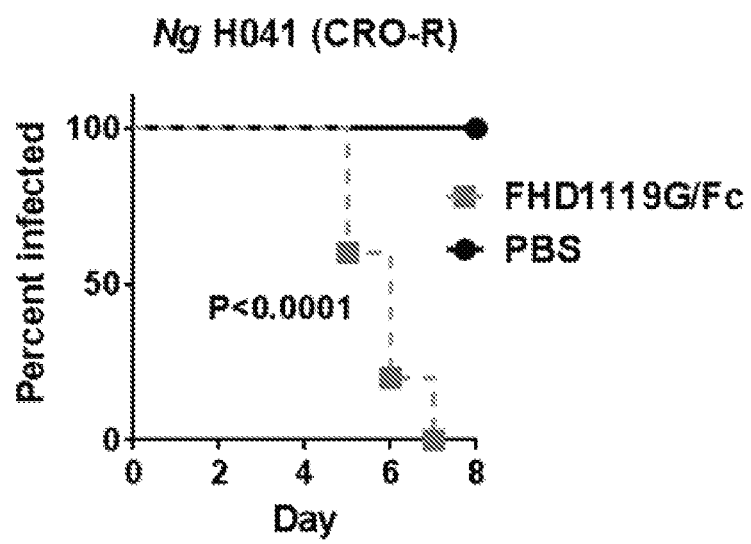
FIGS. 11A-C. Efficacy of FHD1119G/Fc against ceftriaxone-resistant (CRO-R) strain H041. BALB/c mice (n=10/group) were infected with ~$10^6$ CFU of Ng and treated daily intravaginally with PBS (vehicle control) or FHD1119G/human IgG1 Fc (10 µg/day). Vaginal swabs were obtained daily to enumerate viable CFUs. A. Kaplan Meier curve shows time to clearance (Mantel-Cox analysis). B. $\log_{10}$ CFU versus time is shown. C. Bacterial burdens consolidated over time (Area Under Curve ($\log_{10}$ CFU) analysis are shown (comparisons made by Mann-Whitney U test).
Figure 11B:
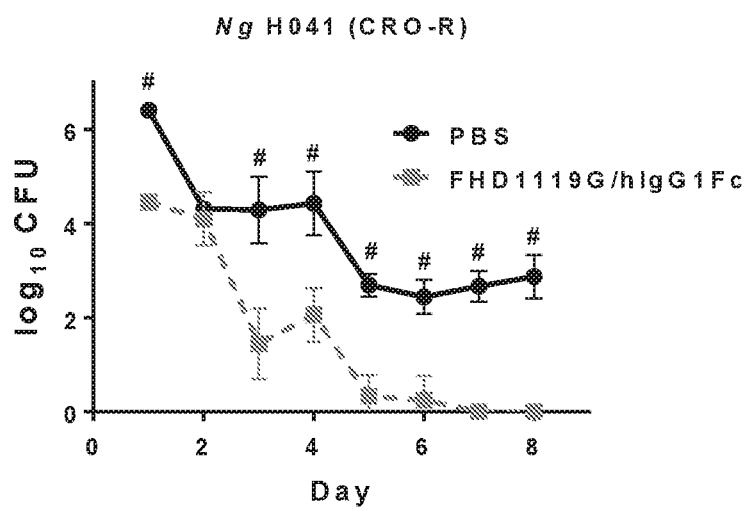
Figure 11C:
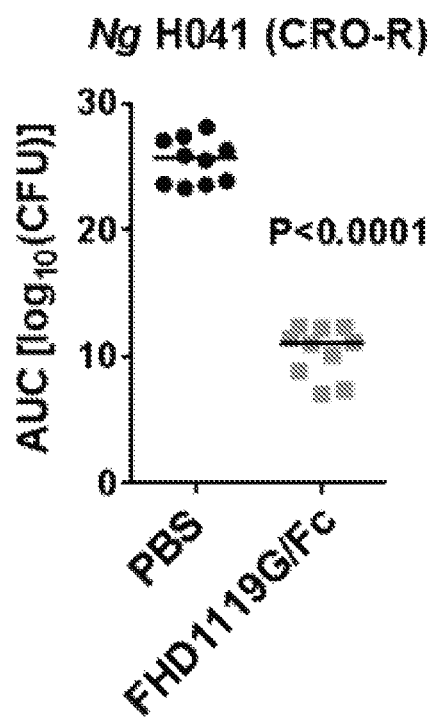

The efficacy of FHD1119G/human IgG1 Fc was tested in the mouse vaginal colonization model. Mice were infected with ~$10^6$ CFU of strain FA1090 or ceftriaxone-resistant (CRO-R) strain H04 and were given either 10 µg of FHD1119G/human IgG1 Fc daily intravaginally (n=10 mice) or PBS as a vehicle control (n=10). As shown in FIG. 10, the groups that received FHD1119G/human IgG1 Fc cleared either infection faster (FIG. 10A; median time to clearance was 5 days, versus 9 days in the control group; P<0.0001; clearance times were compared between groups using Mantel-Cox analysis; FIG. 11A; median time to clearance was 6 days, while none of the mice in the control group were cleared by 8 days; P<0.0001; clearance times were compared between groups using Mantel-Cox analysis;). Two-way ANOVA indicated significant differences between the two groups comparing FHD1119G/human IgG1 Fc and PBS-treated groups (FIG. 10B and FIG. 11B); the main effect for time, log 10 CFU and the interaction between time and log 10 CFU were significant in both instances (P<0.0001); *, P<0.05; **, P<0.01; #, P<0.0001 by Sidak's test at the indicated time points). A significant difference in the Mean Areas Under the Curve (mean AUCs) (log 10 CFU versus time) between the treated and control groups was also observed (P<0.0001; FIG. 10C and FIG. 11C).

REFERENCES

1. Rossolini, G. M., F. Arena, P. Pecile, and S. Pollini. 2014. Update on the antibiotic resistance crisis. $Curr$ $Opin$ $Pharmacol$ 18C: 56-60.
2. Walker, B., S. Barrett, S. Polasky, V. Galaz, C. Folke, G. Engstrom, F. Ackerman, K. Arrow, S. Carpenter, K. Chopra, G. Daily, P. Ehrlich, T. Hughes, N. Kautsky, S. Levin, K. G. Maler, J. Shogren, J. Vincent, T. Xepapadeas, and A. de Zeeuw. 2009. Environment. Looming global-scale failures and missing institutions. $Science$ 325: 1345-1346.
3. Unemo, M., and W. M. Shafer. 2014. Antimicrobial resistance in $Neisseria$ $gonorrhoeae$ in the 21st century: past, evolution, and future. $Clin$ $Microbiol$ $Rev$ 27: 587-613.
4. Camara, J., J. Serra, J. Ayats, T. Bastida, D. Carnicer-Pont, A. Andreu, and C. Ardanuy. 2012. Molecular characterization of two high-level ceftriaxone-resistant $Neisseria$ $gonorrhoeae$ isolates detected in Catalonia, Spain. $J$ $Antimicrob$ $Chemother$ 67: 1858-1860.
5. CDC. 2013. Antibiotic resistance threats in the United States, 2013. Department of Health and Human Services, Centers for Disease Control and Prevention.
6. Lahra, M. M., N. Ryder, and D. M. Whiley. 2014. A new multidrug-resistant strain of $Neisseria$ $gonorrhoeae$ in Australia. $N$ $Engl$ $J$ $Med$ 371: 1850-1851.
7. Ohnishi, M., D. Golparian, K. Shimuta, T. Saika, S. Hoshina, K. Iwasaku, S. Nakayama, J. Kitawaki, and M. Unemo. 2011. Is $Neisseria$ $gonorrhoeae$ initiating a future era of untreatable gonorrhea?: detailed characterization of the first strain with high-level resistance to ceftriaxone. $Antimicrob$ $Agents$ $Chemother$ 55: 3538-3545.
8. Laga, M., A. Manoka, M. Kivuvu, B. Malele, M. Tuliza, N. Nzila, J. Goeman, F. Behets, V. Batter, M. Alary, W. L. Heyward, R. W. Ryder, and P. Piot. 1993. Non-ulcerative sexually transmitted diseases as risk factors for HIV-1 transmission in women: results from a cohort study [see comments]. $Aids$ 7: 95-102.
9. Laga, M., N. Nzila, and J. Goeman. 1991. The interrelationship of sexually transmitted diseases and HIV infection: implications for the control of both epidemics in Africa. $Aids$ 5 Suppl 1: S55-63.
10. Ricklin, D., G. Hajishengallis, K. Yang, and J. D. Lambris. 2010. Complement: a key system for immune surveillance and homeostasis. $Nat$ $Immunol$ 11: 785-797.
11. Blom, A. M., T. Hallstrom, and K. Riesbeck. 2009. Complement evasion strategies of pathogens-acquisition of inhibitors and beyond. $Mol$ $Immunol$ 46: 2808-2817.
12. Kraiczy, P., and R. Wurzner. 2006. Complement escape of human pathogenic bacteria by acquisition of complement regulators. $Mol$ $Immunol$ 43: 31-44.
13. Wurzner, R. 1999. Evasion of pathogens by avoiding recognition or eradication by complement, in part via molecular mimicry. $Mol$ $Immunol$ 36: 249-260.
14. Pangburn, M. K., R. D. Schreiber, and H. J. Muller-Eberhard. 1977. Human complement C3b inactivator: isolation, characterization, and demonstration of an absolute requirement for the serum protein betalH for cleavage of C3b and C4b in solution. $J$ $Exp$ $Med$ 146: 257-270.
15. Fearon, D. T., and K. F. Austen. 1977. Activation of the alternative complement pathway due to resistance of zymosan-bound amplification convertase to endogenous regulatory mechanisms. *Proc Natl Acad Sci USA* 74: 1683-1687.
16. Weiler, J. M., M. R. Daha, K. F. Austen, and D. T. Fearon. 1976. Control of the amplification convertase of complement by the plasma protein betalH. *Proc Natl Acad Sci USA* 73: 3268-3272.
17. Whaley, K., and S. Ruddy. 1976. Modulation of the alternative complement pathways by beta 1H globulin. *J Exp Med* 144: 1147-1163.
18. Ripoche, J., A. J. Day, T. J. Harris, and R. B. Sim. 1988. The complete amino acid sequence of human complement factor H. *Biochem J* 249: 593-602.
19. Sharma, A. K., and M. K. Pangburn. 1996. Identification of three physically and functionally distinct binding sites for C3b in human complement factor H by deletion mutagenesis. *Proc Natl Acad Sci USA* 93: 10996-11001.
20. Apicella, M. A., R. E. Mandrell, M. Shero, M. Wilson, J. M. Griffiss, G. F. Brooks, C. Fenner, C. F. Breen, and P. A. Rice. 1990. Modification by sialic acid of *Neisseria gonorrhoeae* lipooligosaccharide epitope expression in human urethral exudates: an immunoelectron microscopic analysis. *J Infect Dis* 162: 506-512.
21. Parsons, N. J., A. Curry, A. J. Fox, D. M. Jones, J. A. Cole, and H. Smith. 1992. The serum resistance of gonococci in the majority of urethral exudates is due to sialylated lipopolysaccharide seen as a surface coat. *FEMS Microbiol Lett* 69: 295-299.
22. Gulati, S., A. Cox, L. A. Lewis, F. S. Michael, J. Li, R. Boden, S. Ram, and P. A. Rice. 2005. Enhanced factor H binding to sialylated Gonococci is restricted to the sialylated lacto-N-neotetraose lipooligosaccharide species: implications for serum resistance and evidence for a bifunctional lipooligosaccharide sialyltransferase in Gonococci. *Infect Immun* 73: 7390-7397.
23. Ngampasutadol, J., S. Ram, S. Gulati, S. Agarwal, C. Li, A. Visintin, B. Monks, G. Madico, and P. A. Rice. 2008. Human Factor H Interacts Selectively with *Neisseria gonorrhoeae* and Results in Species-Specific Complement Evasion. *J Immunol* 180: 3426-3435.
24. Ram, S., A. K. Sharma, S. D. Simpson, S. Gulati, D. P. McQuillen, M. K. Pangburn, and P. A. Rice. 1998. A novel sialic acid binding site on factor H mediates serum resistance of sialylated *Neisseria gonorrhoeae*. *J Exp Med* 187: 743-752.
25. Madico, G., J. Ngampasutadol, S. Gulati, U. Vogel, P. A. Rice, and S. Ram. 2007. Factor H Binding and Function in Sialylated Pathogenic Neisseriae is Influenced by Gonococcal, but Not Meningococcal, Porin. *J Immunol* 178: 4489-4497.
26. Ram, S., D. P. McQuillen, S. Gulati, C. Elkins, M. K. Pangburn, and P. A. Rice. 1998. Binding of complement factor H to loop 5 of porin protein 1A: a molecular mechanism of serum resistance of nonsialylated *Neisseria gonorrhoeae*. *J Exp Med* 188: 671-680.
27. Shaughnessy, J., S. Ram, A. Bhattacharjee, J. Pedrosa, C. Tran, G. Horvath, B. Monks, A. Visintin, T. S. Jokiranta, and P. A. Rice. 2011. Molecular characterization of the interaction between sialylated *Neisseria gonorrhoeae* and factor H. *J Biol Chem* 286: 22235-22242.
28. Blaum, B. S., J. P. Hannan, A. P. Herbert, D. Kavanagh, D. Uhrin, and T. Stehle. 2015. Structural basis for sialic acid-mediated self-recognition by complement factor H. *Nat Chem Biol* 11: 77-83.
29. Kajander, T., M. J. Lehtinen, S. Hyvarinen, A. Bhattacharjee, E. Leung, D. E. Isenman, S. Meri, A. Goldman, and T. S. Jokiranta. 2011. Dual interaction of factor H with C3d and glycosaminoglycans in host-nonhost discrimination by complement. *Proc Natl Acad Sci USA* 108: 2897-2902.
30. Martin, I. M., C. A. Ison, D. M. Aanensen, K. A. Fenton, and B. G. Spratt. 2004. Rapid sequence-based identification of gonococcal transmission clusters in a large metropolitan area. *J Infect Dis* 189: 1497-1505.
31. Lewis, L. A., S. Ram, A. Prasad, S. Gulati, S. Getzlaff, A. M. Blom, U. Vogel, and P. A. Rice. 2008. Defining targets for complement components C4b and C3b on the pathogenic neisseriae. *Infect Immun* 76: 339-350.
32. McQuillen, D. P., S. Gulati, and P. A. Rice. 1994. Complement-mediated bacterial killing assays. *Methods Enzymol* 236: 137-147.
33. Ray, T. D., L. A. Lewis, S. Gulati, P. A. Rice, and S. Ram. 2011. Novel blocking human IgG directed against the pentapeptide repeat motifs of *Neisseria meningitidis* Lip/H.8 and Laz lipoproteins. *J Immunol* 186: 4881-4894.
34. Visintin, A., K. A. Halmen, E. Latz, B. G. Monks, and D. T. Golenbock. 2005. Pharmacological inhibition of endotoxin responses is achieved by targeting the TLR4 coreceptor, MD-2. *J Immunol* 175: 6465-6472.
35. Shaughnessy, J., D. M. Vu, R. Punjabi, J. Serra-Pladevall, R. B. DeOliveira, D. M. Granoff, and S. Ram. 2014. Fusion protein comprising factor H domains 6 and 7 and human IgG1 Fc as an antibacterial immunotherapeutic. *Clin Vaccine Immunol* 121: 1452-1459.
36. Gulati, S., S. Agarwal, S. Vasudhev, P. A. Rice, and S. Ram. 2012. Properdin is critical for antibody-dependent bactericidal activity against *Neisseria gonorrhoeae* that recruit C4b-binding protein. *J Immunol* 188: 3416-3425.
37. Ferreira, V. P., A. P. Herbert, C. Cortes, K. A. McKee, B. S. Blaum, S. T. Esswein, D. Uhrin, P. N. Barlow, M. K. Pangburn, and D. Kavanagh. 2009. The binding of factor H to a complex of physiological polyanions and C3b on cells is impaired in atypical hemolytic uremic syndrome. *J Immunol* 182: 7009-7018.
38. Sarantis, H., and S. D. Gray-Owen. 2012. Defining the roles of human carcinoembryonic antigen-related cellular adhesion molecules during neutrophil responses to *Neisseria gonorrhoeae*. *Infect Immun* 80: 345-358.
39. Jerse, A. E., H. Wu, M. Packiam, R. A. Vonck, A. A. Begum, and L. E. Garvin. 2011. Estradiol-Treated Female Mice as Surrogate Hosts for *Neisseria gonorrhoeae* Genital Tract Infections. *Front Microbiol* 2: 107.
40. Brinkman-Van der Linden, E. C., E. R. Sjoberg, L. R. Juneja, P. R. Crocker, N. Varki, and A. Varki. 2000. Loss of N-glycolylneuraminic acid in human evolution. Implications for sialic acid recognition by siglecs. *J Biol Chem* 275: 8633-8640.
41. Chou, H. H., T. Hayakawa, S. Diaz, M. Krings, E. Indriati, M. Leakey, S. Paabo, Y. Satta, N. Takahata, and A. Varki. 2002. Inactivation of CMP-N-acetylneuraminic acid hydroxylase occurred prior to brain expansion during human evolution. *Proc Natl Acad Sci USA* 99: 11736-11741.
42. Chou, H. H., H. Takematsu, S. Diaz, J. Iber, E. Nickerson, K. L. Wright, E. A. Muchmore, D. L. Nelson, S. T. Warren, and A. Varki. 1998. A mutation in human CMP-sialic acid hydroxylase occurred after the Homo-Pan divergence. *Proc Natl Acad Sci USA* 95: 11751-11756.
43. Davies, L. R., and A. Varki. 2015. Why Is N-Glycolylneuraminic Acid Rare in the Vertebrate Brain? *Top Curr Chem* 366: 31-54.
44. Gulati, S., B. Zheng, G. W. Reed, X. Su, A. D. Cox, F. St Michael, J. Stupak, L. A. Lewis, S. Ram, and P. A. Rice.

45. Jokiranta, T. S., J. Hellwage, V. Koistinen, P. F. Zipfel, and S. Meri. 2000. Each of the three binding sites on complement factor H interacts with a distinct site on C3b. *J Biol Chem* 275: 27657-27662.
46. Schmidt, C. Q., A. P. Herbert, D. Kavanagh, C. Gandy, C. J. Fenton, B. S. Blaum, M. Lyon, D. Uhrin, and P. N. Barlow. 2008. A new map of glycosaminoglycan and C3b binding sites on factor H. *J Immunol* 181: 2610-2619.
47. Manuelian, T., J. Hellwage, S. Meri, J. Caprioli, M. Noris, S. Heinen, M. Jozsi, H. P. Neumann, G. Remuzzi, and P. F. Zipfel. 2003. Mutations in factor H reduce binding affinity to C3b and heparin and surface attachment to endothelial cells in hemolytic uremic syndrome. *J Clin Invest* 111: 1181-1190.
48. de Cordoba, S. R., A. Tortajada, C. L. Harris, and B. P. Morgan. 2012. Complement dysregulation and disease: from genes and proteins to diagnostics and drugs. *Immunobiology* 217: 1034-1046.
49. Nester, C. M., T. Barbour, S. R. de Cordoba, M. A. Dragon-Durey, V. Fremeaux-Bacchi, T. H. Goodship, D. Kavanagh, M. Noris, M. Pickering, P. Sanchez-Corral, C. Skerka, P. Zipfel, and R. J. Smith. 2015. Atypical aHUS: State of the art. *Mol Immunol* 67: 31-42.
50. Rodriguez, E., P. M. Rallapalli, A. J. Osborne, and S. J. Perkins. 2014. New functional and structural insights from updated mutational databases for complement factor H, Factor I, membrane cofactor protein and C3. *Biosci Rep* 34.
51. McQuillen, D. P., S. Gulati, S. Ram, A. K. Turner, D. B. Jani, T. C. Heeren, and P. A. Rice. 1999. Complement processing and immunoglobulin binding to *Neisseria gonorrhoeae* determined in vitro simulates in vivo effects. *J Infect Dis* 179: 124-135.
52. Li, S., X. Su, W. Le, F. Jiang, B. Wang, and P. A. Rice. 2014. Antimicrobial susceptibility of *Neisseria gonorrhoeae* isolates from symptomatic men attending the Nanjing sexually transmitted diseases clinic (2011-2012): genetic characteristics of isolates with reduced sensitivity to ceftriaxone. *BMC Infect Dis* 14: 622.
53. Gray-Owen, S. D., C. Dehio, A. Haude, F. Grunert, and T. F. Meyer. 1997. CD66 carcinoembryonic antigens mediate interactions between Opa-expressing *Neisseria gonorrhoeae* and human polymorphonuclear phagocytes. *EMBO J* 16: 3435-3445.
54. WHO. 2012. Global action plan to control the spread and impact of antimicrobial resistance in *Neisseria gonorrhoeae*. World Health Organization (WHO), Department of Reproductive Health and Research. 1-36.
55. Wu, H., and A. E. Jerse. 2006. Alpha-2,3-sialyltransferase enhances *Neisseria gonorrhoeae* survival during experimental murine genital tract infection. *Infect Immun* 74: 4094-4103.
56. Wu, H., W. M. Shafer, and A. E. Jerse. 2012. Relative importance of LOS sialylation and the MtrC-MtrD-MtrE active efflux pump in gonococcal evasion of host innate defenses. In *XVIIIth International Pathogenic Neisseria Conference*, Wuerzburg, Germany. 364.
57. Arko, R. J., C. Y. Chen, W. O. Schalla, S. K. Sarafian, C. L. Taylor, J. S. Knapp, and S. A. Morse. 1991. Binding of S protein by *Neisseria gonorrhoeae* and potential role in invasion. *J Clin Microbiol* 29: 70-75.
58. Dehio, M., 0. G. Gomez-Duarte, C. Dehio, and T. F. Meyer. 1998. Vitronectin-dependent invasion of epithelial cells by *Neisseria gonorrhoeae* involves alpha(v) integrin receptors. *FEBS Lett* 424: 84-88.
59. Duensing, T. D., and J. P. van Putten. 1997. Vitronectin mediates internalization of *Neisseria gonorrhoeae* by Chinese hamster ovary cells. *Infect Immun* 65: 964-970.
60. Gomez-Duarte, O. G., M. Dehio, C. A. Guzman, G. S. Chatwal, C. Dehio, and T. F. Meyer. 1997. Binding of vitronectin to opa-expressing *Neisseria gonorrhoeae* mediates invasion of HeLa cells. *Infect Immun* 65: 3857-3866.
61. Meri, T., H. Amdahl, M. J. Lehtinen, S. Hyvarinen, J. V. McDowell, A. Bhattacharjee, S. Meri, R. Marconi, A. Goldman, and T. S. Jokiranta. 2013. Microbes bind complement inhibitor factor H via a common site. *PLoS Pathog* 9: e1003308.
62. Lewis, L. A., S. Gulati, E. Burrowes, B. Zheng, S. Ram, and P. A. Rice. 2015. alpha-2,3-Sialyltransferase Expression Level Impacts the Kinetics of Lipooligosaccharide Sialylation, Complement Resistance, and the Ability of *Neisseria gonorrhoeae* to Colonize the Murine Genital Tract. *MBio* 6.
63. Yang, Q. L., and E. C. Gotschlich. 1996. Variation of gonococcal lipooligosaccharide structure is due to alterations in poly-G tracts in lgt genes encoding glycosyl transferases. *J Exp Med* 183: 323-327.
64. Schneider, H., J. M. Griffiss, J. W. Boslego, P. J. Hitchcock, K. M. Zahos, and M. A. Apicella. 1991. Expression of paragloboside-like lipooligosaccharides may be a necessary component of gonococcal pathogenesis in men. *J Exp Med* 174: 1601-1605.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion polypeptide consisting of Factor H (FH) domains 18-20 (FH18-20) linked via a linker to a human IgG1 Fc region, wherein the FH18-20 has a mutation at position 1119 in domain 19, and wherein the linker comprises at least two additional amino acids between the FH domain and the human IgG1 Fc region.

2. The fusion polypeptide of claim 1, wherein the linker comprises at least one glycine or one alanine.

3. The fusion polypeptide of claim 1, wherein the linker comprises GAAGG (SEQ ID NO: 1) or AAAGG (SEQ ID NO:2).

4. The fusion polypeptide of claim 1, wherein the FH18-20 has a mutation of D to G at position 1119 in domain 19.

5. A pharmaceutical composition comprising the fusion polypeptide of claim 1, and a pharmaceutically acceptable carrier.

6. A method of treating a disorder associated with a Factor H-binding pathogen in a subject, the method comprising administering a therapeutically effective amount of a fusion polypeptide of claim 1.

7. The method of claim 6, wherein the disorder is a pathogen-associated infection or an inflammatory condition.

8. The method of claim 6, wherein the pathogen is selected from the group consisting of bacteria, fungi, viruses, spirochetes, and parasites.

9. The method of claim 8, wherein the bacterium is selected from the group consisting of *P. aeruginosa, S. pneumoniae, Y. pestis, E. coli, S. typhimurium, N. meningitidis, N. gonorrhoeae, H. influenza* and *S. aureus*; the fungus is selected from the group consisting of *Aspergillus fumigatus, Candida albicans*, and other zymosan-containing fungi; the spirochete is *Borrelia burgdorferi* or *Treponema pallidum*; or the parasite is *Plasmodium berghei* or *Plasmodium falciparum*.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: linker sequence

```
<400> SEQUENCE: 1

Gly Ala Ala Gly Gly
1               5

<210> SEQ ID NO 2
<211> LENGTH: 5
<212> TYPE: PRT
<213> ORGANISM: Artificial Sequence
<220> FEATURE:
<223> OTHER INFORMATION: linker sequence

<400> SEQUENCE: 2

Ala Ala Ala Gly Gly
1               5

<210> SEQ ID NO 3
<211> LENGTH: 184
<212> TYPE: PRT
<213> ORGANISM: Homo sapiens
<220> FEATURE:
<221> NAME/KEY: misc_feature
<222> LOCATION: (72)..(72)
<223> OTHER INFORMATION: Xaa can be Asp, Gly, Ala, Ile, Leu, Pro or Ser

<400> SEQUENCE: 3

Cys Val Asn Pro Pro Thr Val Gln Asn Ala Tyr Ile Val Ser Arg Gln
1               5                   10                  15

Met Ser Lys Tyr Pro Ser Gly Glu Arg Val Arg Tyr Gln Cys Arg Ser
            20                  25                  30

Pro Tyr Glu Met Phe Gly Asp Glu Glu Val Met Cys Leu Asn Gly Asn
        35                  40                  45

Trp Thr Glu Pro Pro Gln Cys Lys Asp Ser Thr Gly Lys Cys Gly Pro
    50                  55                  60

Pro Pro Pro Ile Asp Asn Gly Xaa Ile Thr Ser Phe Pro Leu Ser Val
65                  70                  75                  80

Tyr Ala Pro Ala Ser Ser Val Glu Tyr Gln Cys Gln Asn Leu Tyr Gln
                85                  90                  95

Leu Glu Gly Asn Lys Arg Ile Thr Cys Arg Asn Gly Gln Trp Ser Glu
            100                 105                 110

Pro Pro Lys Cys Leu His Pro Cys Val Ile Ser Arg Glu Ile Met Glu
        115                 120                 125

Asn Tyr Asn Ile Ala Leu Arg Trp Thr Ala Lys Gln Lys Leu Tyr Ser
    130                 135                 140

Arg Thr Gly Glu Ser Val Glu Phe Val Cys Lys Arg Gly Tyr Arg Leu
145                 150                 155                 160

Ser Ser Arg Ser His Thr Leu Arg Thr Thr Cys Trp Asp Gly Lys Leu
                165                 170                 175

Glu Tyr Pro Thr Cys Ala Lys Arg
            180

<210> SEQ ID NO 4
<211> LENGTH: 238
<212> TYPE: PRT
<213> ORGANISM: Mus musculus

<400> SEQUENCE: 4

Ala Ala Ala Gly Gly Glu Pro Arg Gly Pro Thr Ile Lys Pro Cys Pro
1               5                   10                  15

Pro Cys Lys Cys Pro Ala Pro Asn Leu Leu Gly Gly Pro Ser Val Phe
            20                  25                  30
```

-continued

```
Ile Phe Pro Pro Lys Ile Lys Asp Val Leu Met Ile Ser Leu Ser Pro
         35                  40                  45
Ile Val Thr Cys Val Val Val Asp Val Ser Glu Asp Asp Pro Asp Val
 50                  55                  60
Gln Ile Ser Trp Phe Val Asn Asn Val Glu Val His Thr Ala Gln Thr
 65                  70                  75                  80
Gln Thr His Arg Glu Asp Tyr Asn Ser Thr Leu Arg Val Val Ser Ala
             85                  90                  95
Leu Pro Ile Gln His Gln Asp Trp Met Ser Gly Lys Glu Phe Lys Cys
             100                 105                 110
Lys Val Asn Asn Lys Asp Leu Pro Ala Pro Ile Glu Arg Thr Ile Ser
         115                 120                 125
Lys Pro Lys Gly Ser Val Arg Ala Pro Gln Val Tyr Val Leu Pro Pro
     130                 135                 140
Pro Glu Glu Glu Met Thr Lys Lys Gln Val Thr Leu Thr Cys Met Val
145                 150                 155                 160
Thr Asp Phe Met Pro Glu Asp Ile Tyr Val Glu Trp Thr Asn Asn Gly
             165                 170                 175
Lys Thr Glu Leu Asn Tyr Lys Asn Thr Glu Pro Val Leu Asp Ser Asp
         180                 185                 190
Gly Ser Tyr Phe Met Tyr Ser Lys Leu Arg Val Glu Lys Lys Asn Trp
     195                 200                 205
Val Glu Arg Asn Ser Tyr Ser Cys Ser Val Val His Glu Gly Leu His
 210                 215                 220
Asn His His Thr Thr Lys Ser Phe Ser Arg Thr Pro Gly Lys
225                 230                 235
```

<210> SEQ ID NO 5
<211> LENGTH: 330
<212> TYPE: PRT
<213> ORGANISM: Homo sapiens
<220> FEATURE:
<221> NAME/KEY: misc_feature
<222> LOCATION: (239)..(239)
<223> OTHER INFORMATION: Xaa can be Asp or Glu
<220> FEATURE:
<221> NAME/KEY: misc_feature
<222> LOCATION: (241)..(241)
<223> OTHER INFORMATION: Xaa can be any Leu or Met

<400> SEQUENCE: 5

```
Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
             85                  90                  95
Lys Val Glu Pro Lys Ser Cys Asp Lys Thr His Thr Cys Pro Pro Cys
         100                 105                 110
Pro Ala Pro Glu Leu Leu Gly Gly Pro Ser Val Phe Leu Phe Pro Pro
     115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 232
<212> TYPE: PRT
<213> ORGANISM: Homo sapiens

<400> SEQUENCE: 6

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

```
<210> SEQ ID NO 7
<211> LENGTH: 37
<212> TYPE: DNA
<213> ORGANISM: Artificial Sequence
<220> FEATURE:
<223> OTHER INFORMATION: Primer D1119G

<400> SEQUENCE: 7
cacctattga caatggggc attacttcat tcccgtt                            37

<210> SEQ ID NO 8
<211> LENGTH: 48
<212> TYPE: DNA
<213> ORGANISM: Artificial Sequence
<220> FEATURE:
<223> OTHER INFORMATION: Primer R1182S

<400> SEQUENCE: 8
attatggaaa attataacat agcattaagc tggacagcca aacagaag               48

<210> SEQ ID NO 9
<211> LENGTH: 47
<212> TYPE: DNA
<213> ORGANISM: Artificial Sequence
<220> FEATURE:
<223> OTHER INFORMATION: Primer W1183R

<400> SEQUENCE: 9
aaaattataa catagcatta aggaggacag ccaaacagaa gctttat                47

<210> SEQ ID NO 10
<211> LENGTH: 35
<212> TYPE: DNA
<213> ORGANISM: Artificial Sequence
<220> FEATURE:
<223> OTHER INFORMATION: Primer R1215G

<400> SEQUENCE: 10
cacgttctca cacattggga acaacatgtt gggat                             35

<210> SEQ ID NO 11
<211> LENGTH: 29
<212> TYPE: DNA
<213> ORGANISM: Artificial Sequence
<220> FEATURE:
<223> OTHER INFORMATION: Primer FH18EcoRI

<400> SEQUENCE: 11
gaattcgtgt gtgaatccgc ccacagtac                                    29

<210> SEQ ID NO 12
<211> LENGTH: 35
<212> TYPE: DNA
<213> ORGANISM: Artificial Sequence
```

```
<220> FEATURE:
<223> OTHER INFORMATION: Primer FH20hIgG1overlapF

<400> SEQUENCE: 12
agcccaaatc ttgtgacaaa actcacacat gccca                              35

<210> SEQ ID NO 13
<211> LENGTH: 32
<212> TYPE: DNA
<213> ORGANISM: Artificial Sequence
<220> FEATURE:
<223> OTHER INFORMATION: Primer FH20hIgG1overlapR

<400> SEQUENCE: 13
gccgcggggg gcgagcccaa atcttgtgac aa                                 32

<210> SEQ ID NO 14
<211> LENGTH: 22
<212> TYPE: DNA
<213> ORGANISM: Artificial Sequence
<220> FEATURE:
<223> OTHER INFORMATION: Primer HIgG1NheI

<400> SEQUENCE: 14
cgggtaaatg agtgctagct gg                                            22
```